US007507871B2

(12) United States Patent
Jacob et al.

(10) Patent No.: US 7,507,871 B2
(45) Date of Patent: Mar. 24, 2009

(54) RAT MODEL OF DIABETIC NEPHROPATHY

(75) Inventors: Howard J. Jacob, Brookfield, WI (US); Richard J. Roman, Brookfield, WI (US); Marcelo Nobrega, Richmond, CA (US)

(73) Assignee: MCW Research Foundation, Inc., Milwaukee, WI (US)

( * ) Notice: Subject to any disclaimer, the term of this patent is extended or adjusted under 35 U.S.C. 154(b) by 111 days.

(21) Appl. No.: 10/625,870

(22) Filed: Jul. 23, 2003

(65) Prior Publication Data

US 2005/0166273 A1 Jul. 28, 2005

Related U.S. Application Data

(60) Provisional application No. 60/398,446, filed on Jul. 25, 2002.

(51) Int. Cl.
*A01K 67/00* (2006.01)
*G01N 33/00* (2006.01)
*C12N 15/00* (2006.01)
*A61K 49/00* (2006.01)

(52) U.S. Cl. .................. 800/9; 800/3; 800/13; 800/22; 514/866; 424/9.2

(58) Field of Classification Search ........................ None
See application file for complete search history.

(56) References Cited

U.S. PATENT DOCUMENTS

| 5,789,652 | A * | 8/1998 | Kawano et al. ................. 800/9 |
| 6,465,714 | B2 | 10/2002 | Luthman et al. |
| 2002/0035733 | A1 | 3/2002 | Luthman et al. |
| 2004/0023567 | A1 | 2/2004 | Koyama et al. |

FOREIGN PATENT DOCUMENTS

| CA | 2389852 | 5/2001 |
| JP | 2003-512852 | 4/2003 |
| WO | WO 01/32126 | 5/2001 |

OTHER PUBLICATIONS

Van Tilburg et al., J Med Genet, 2001, 38: 569-578.*
Barnas et al., Diabetologia, 1997, 40: 327-331.*
Keith et al., Nature Reviews Drug Discovery, 2005, 4: 71-78.*
Kusminski et al., Clinical Science, 2005, 109: 243-256.*
Roep et al., Diabetologia, 2004, 47: 1650-1656.*
Nakamura et al., Diabetes, 1997, 46: 895-899.*
Kawano et al., Diabetes Research and Clinical Practice, 1994, 24 Suppl: S317-S320.*
Sone et al., Trends in Molecular Medicine, 2001, 7: 320-322.*
T. Abe, et al., "Left Ventricular Diastolic Dysfunction in Type 2 Diabetes Mellitus Model Rats," Am. J. Physiol. Hearth Circ. Physiol. 282(1):H138-148, 2002.
J. Chen, et al., "Endothelin Receptor Antagonist Combined with a Calcium Channel Blocker Attenuates Renal Injury in Spontaneous Hypertensive Rats with Diabetes," Chin. Med. J. (Engl.) 115(7):972-978. 2002.

J.T. Cheng, et al., "Stimulation of Insulin Release in Rats by Die-Huang-Wan, a Herbal Mixture used in Chinese Traditional Medicine," J. Pharm. Pharmacol. 53(2):273-276, 2001.
A.M. Cohen, et al., "the Cohen Diabetic (Non-Insulin-Dependent) Hypertensive Rat Model. Description of the Model and Pathologic Findings," Am. J. Hypertens. 6(12):989-995, 1993.
Y. Gu, et al., "The Effects of Endothelin Blockade on Renal Expression of Angiotensin II Type 1 Receptor in Diabetic Hypertensive Rats," Zhonghua Yi Xue Za Zhi 82(1):10-13, 2002.
S. Hoshi, et al., "Podocyte Injury Promotes Progressive Nephropathy in Zucker Diabetic Fatty Rats," Lab. Invest. 82(1):25-35, 2002.
N. Hosomi, et al., "Vascular Proliferation and Transforming Growth Factor-beta Expression in Pre- and Early Stage of Diabetes Mellitus in Otsuka Long-Evans Tokushima Fatty Rats," Atherosclerosis 162(1):69-76, 2002.
U. Janssen, et al., "Hypertension Superinmposed on Type II Diabetes in Goto Kakizaki Rats Induces Progressive Nephropathy," Kidney Int. 63(6):2162-2170, 2003.
S. Jesmin, et al., "Long-acting Calcium Channel Blocker Benidipine Suppresses Expression of Angiogenic Growth Factors and Prevents Cardiac Remodelling in a Type II Diabetic Rat Model," Diabetologia 45(3):402-415, 2002.
N. Kanemoto, et al., "Genetic Analysis of Pancreatic Duct Hyperplasia in Otsuka Long-Evans Tokushima Fatty Rats: Possible Association with a Region on Rat Chromosome 14 that includes the Disrupted Cholecystokinin-A Receptor Gene," Pathol. Int. 51(3):133-139, 2001.
P.J. Kaisaki, et al., "Localization, cDNA Sequence and Genomic Organization of the Rat Seipin Gene (Bscl2) and Sequence Analysis in Inbred Rat Models of Type 2 Diabetes Mellitus," Cytogenet. Genome Res. 98(1):71-74, 2002.
H. Masuda, "Effects of Temocapril on the Prevention of Early Diabetic Nephropathy in OLETF Rat, an Animal Model for Type 2 Diabetes," Hokkaido Igaku Zasshi 77(5):419-428, 2002.
S.A. Mifsud, et al., "Podocyte Foot Process Broadening in Experimental Diabetic Nephropathy: Amelioration with Renin-Angiotensin Blockade," Diabetologia 44(7):878-882, 2001.
M. d Aguiar Nobrega, "Distinct Genetic Regulation of the Onset and Progression of Diabetes and Renal Disease in the GOTO-Kakizaki (GK) Rat," pp. 1-275, Apr. 2001.
S.H. Park, et al., "Neointimal Hyperplasia After Arterial Injury is Increased in a Rat Model of Non-insulin-dependent Diabetes Millitus," Circulation 104(7):815-819, 2001.

(Continued)

*Primary Examiner*—Joseph Woitach
*Assistant Examiner*—Ileana Popa
(74) *Attorney, Agent, or Firm*—Quarles & Brady, LLP

(57) ABSTRACT

A rat model of diabetic nephropathy is disclosed. In another embodiment of the invention, a method of evaluating a test compound's effect of diabetic nephropathy is disclosed. In one embodiment, this method comprises the steps of (a) exposing the test compound to the rat of claim 1, wherein the rat would develop progressive proteinuria and glomerulosclerosis leading to diabetic nephropathy in the absence of the test compound, and (b) comparing the rat's development of diabetic nephropathy with a control T2DN mimic rat that has not been exposed to the test compound.

10 Claims, 12 Drawing Sheets

(5 of 12 Drawing Sheet(s) Filed in Color)

OTHER PUBLICATIONS

S.K. Park and S.K. Kang, "Renal Function and Hemodynamic Study in Obese Zucker Rats," Korean J. Intern. Med. 10(1):48-53, 1995.

C. Plachot, et al., "Impaired Beta-cell Regeneration After Partial Pancreatectomy in the Adult Goto-Kakizaki Rat, a Spontaneous Model of Tyep II Diabetes," Histochem. Cell Biol. 116(2):131-139, 2001.

P. Serradas, et al., "Fetal Insulin-like Growth Factor-2 Production is Impaired in the GK Rat Model of Type 2 Diabetes," Diabetes 51(2):392-397, 2002.

K. Sugimoto, et al., "Renal Protective Effect of YM598, a Selective Endothelin ET(A) Receptor Antagonist, against Diabetic Nephropathy in OLETF Rats," Eur. J. Pharmacol. 450(2):183-189, 2002.

Y. Sun, et al., "the Biomimetic [Cr(3)O(O(2)CCH(2)CH(3))(6)(H(2)O)(3)](+) decreases Plasma Insulin, Cholesterol, and Triglycerides in Healthy and Type II Diabetic Rats but not Type I Diabetic Rats," J. Biol. Inorg. Chem. 7(7-8):852-862, 2002.

M.T. Velasque, et al., "Leptin and its Relation to Obesity and Insulin in the SHR/N-corpulent Rat, a Model of Type II Diabetes Mellitus," Int. J. Exp. Diabetes Res. 2(3):217-223, 2001.

S.N. Wang, et al., "Role of Glomerular Ultrafiltration of Growth Factors in Progressive Interstitial Fibrosis in Diabetic Nephropathy," Kidney Int. 57(3):1002-1014, 2000.

A.B. Fogo, "Diabetic Nephropathy: It's in the Numbers," Kidney Internat. 61:2274-2275, 2002.

M. Yu, et al., "20-Hydroxyeicosatetraenoic Acid (20-HETE): Structural Determinants for Renal Vasoconstriction," Bioorganic Med. Chem. 11:2803-2821, 2003.

Nobrega Marcelo A et al., "A new rat model . . . ", Journal of the American Society of Nephrology, vol. 12, No. Program and Abstract Issue, Sep. 2001 pp. 821A-822A.

Broeckel Ulrich et al. "Susceptibility genes . . . " Nephrology Dialysis Transplantation vol. 13, No. 4, Apr. 1998, pp. 840-842.

Galli Joakim et al. "Pathophysiological and genetic characterization . . . ", Diabetes, vol. 48, No. 12, Dec. 1999 pp. 2463-2470.

Brown D. M et al., "Renal Disease Susceptibility . . . ", Nat Genet. Jan. 1996; 12(1):44-51.

Nobrega Marcelo A et al., "Initial Characterization of a rat model . . . ", Diabetes, vol. 53, No. 3, Mar. 2004; pp. 735-742.

* cited by examiner

Figure 1: Comparison of Genotypes of T2DNmimic And GKFL rats on Chromosome 1.

Figure 5
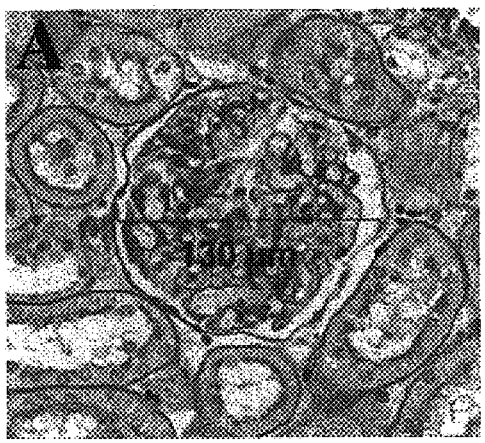 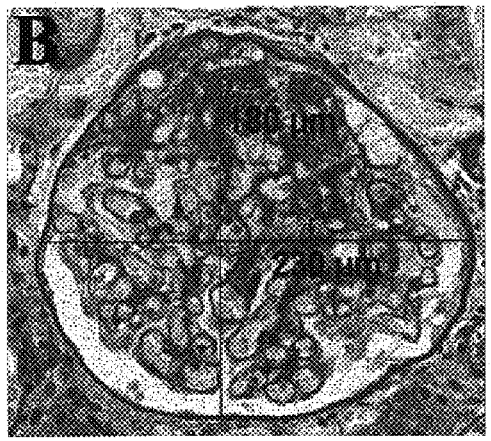
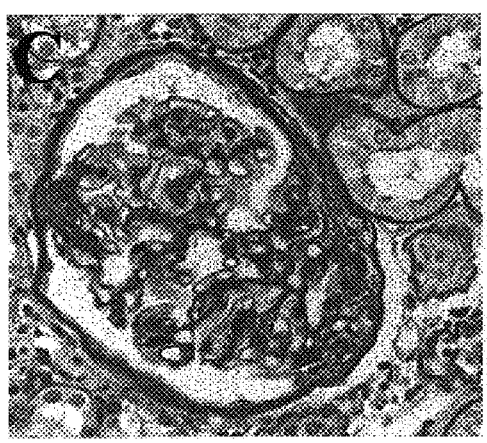 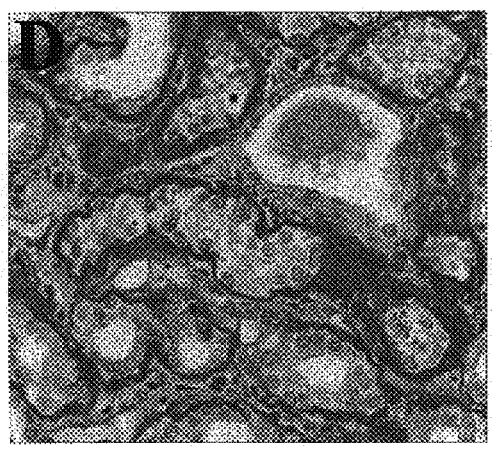
 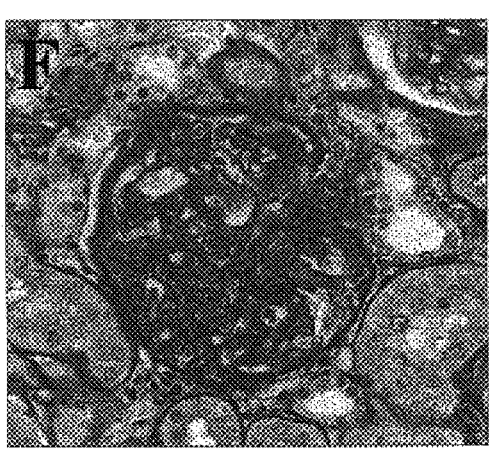

Figure 6
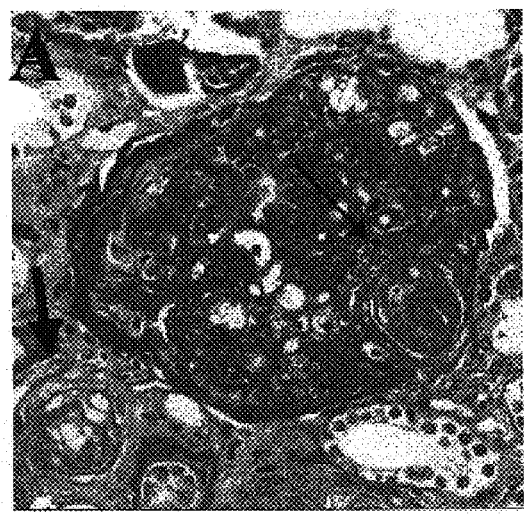
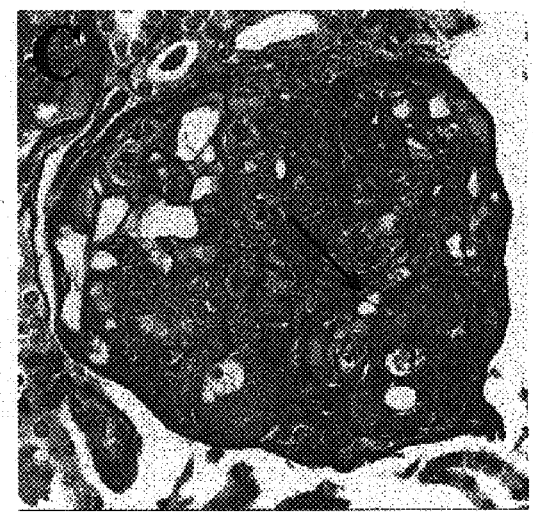

Figure 7: Kimmelsteil-Wilson Lesion in the Glomerulus of a 18 month old T2DNmimic rat.
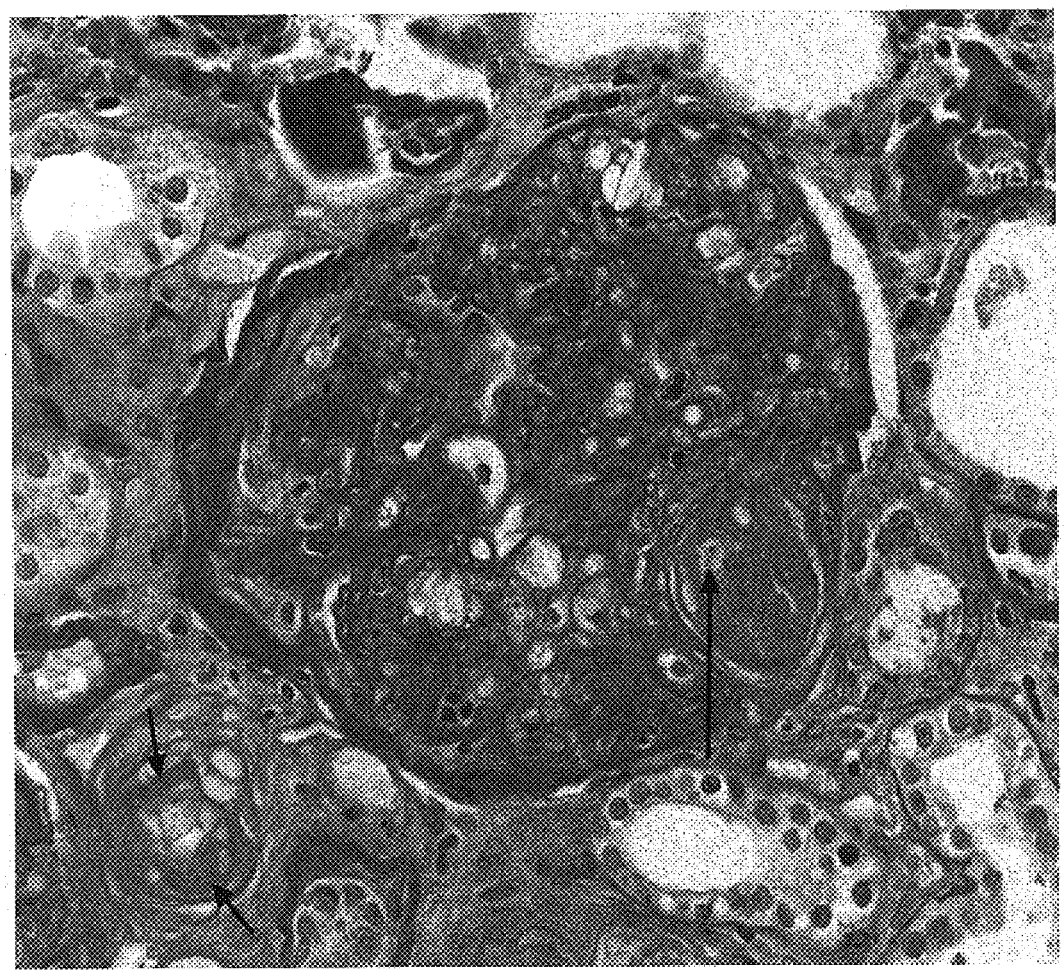

Figure 8: Lack of global glomerulosclerosis or appearance of Kimmelstein Wilson Lesions in Glomeruli of GKFL rats
GKFL Rats 18 months
GKFL Rats 22 months

Figure 11
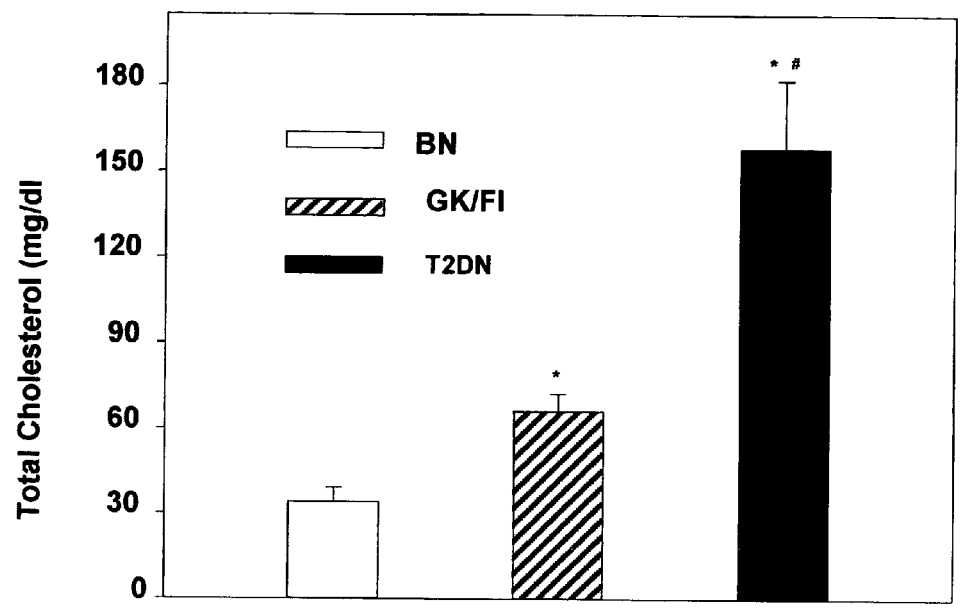
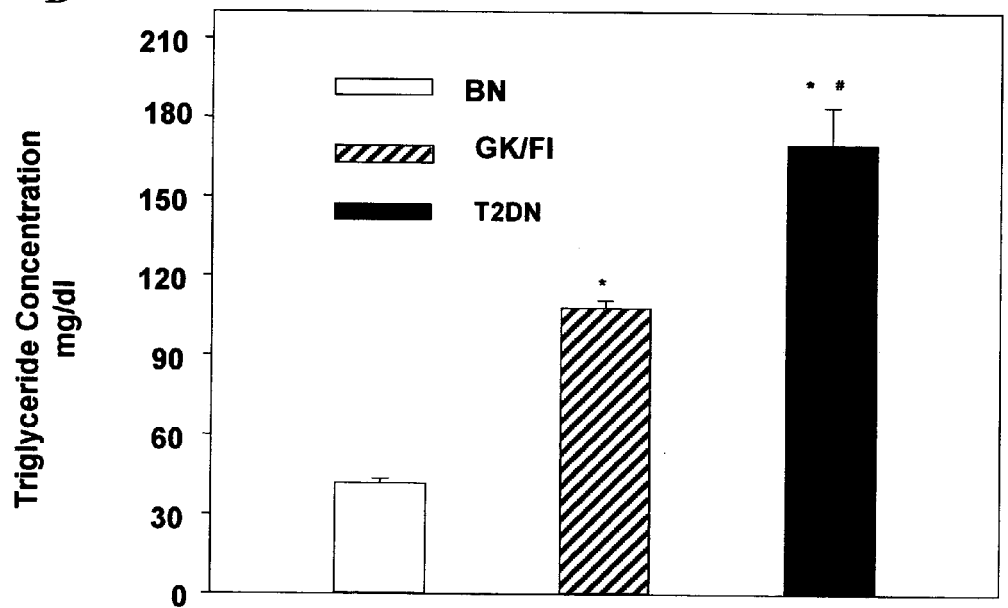

RAT MODEL OF DIABETIC NEPHROPATHY

CROSS-REFERENCE TO RELATED APPLICATION

The application claims priority to U.S. provisional application 60/398,446, filed Jul. 25, 2002, incorporated by reference herein.

STATEMENT REGARDING FEDERALLY SPONSORED RESEARCH OR DEVELOPMENT

BACKGROUND OF THE INVENTION

One of the major morbidity and mortality factors confronted by diabetic patients is an increased risk of developing diabetic nephropathy that often progresses to End-Stage Renal Disease (ESRD) (US Renal Data System: Excerpts from the USRDS 2000 Annual Data Report: Atlas of End-Stage Renal Disease in the United States, *Am. J. Kidney Dis.* 36:S1-S238, 2000; Parving, H. H., et al., "Diabetic Nephropathy," In Brenner and Rector's The Kidney 6$^{th}$ Edition, W. B. Saunders Company, pp. 1731-1773, 2000; Viberti, G., et al., *Joslin's Diabetes, pp.* 691-737, 1992). A long-standing question pertaining to the development of renal disease in diabetes concerns the mechanisms involved in this process. A wealth of data has been generated on possible mechanisms by which diabetes and its ancillary metabolic, hemodynamic, glomerular growth and glomerular cell injury-related alterations may modulate the progression of diabetic nephropathy (Viberti, G., *Kidney Internat.* 55(6):2526-2527, 1999; Sullivan, J. L., *Circulation* 100(12):1260-1263, 1999; Orloff, L. A., et al., *Arch. Surg.* 134(8):889-897, 1999; Lewis, J. and Lewis, E. J., *Sem. Nephrol.* 21(2):124-132, 2001). Nevertheless, the observation that approximately ⅔ of diabetic patients do not develop renal disease indicates that hyperglycemia is a permissive factor in diabetic nephropathy and elevated plasma glucose levels alone do not fully account for renal injury (US Renal Data System: Excerpts from the USRDS 2000 Annual Data Report: Atlas of End-Stage Renal Disease in the United States, *Am. J. Kidney Dis.* 36:S1-S238, 2000). Thus, genetic factors are thought to play a major role in the susceptibility for diabetic nephropathy and there are several clinical and epidemiological studies that strongly support this view (Seaquist, E. R., et al., *New Eng. J. Med.* 320:1161-1165, 1989; Freedman, B. I., et al., *Am. J. Kidney Dis.* 25(5):710-713, 1995).

The complex interplay between diabetes-dependent and independent factors in determining the progression of renal disease could become more amenable to study if there were an adequate animal model which spontaneously develops diabetes and renal lesions that mimic those seen in patients with diabetic nephropathy. However, to date, no rodent model of diabetes has been developed that fully recapitulates the chronology of events and histologic changes in the kidney that are characteristic of patients with diabetic nephropathy. The lack of suitable small animal models for diabetic nephropathy is severely hindering efforts to identify biological markers predictive of diabetes-related ESRD and in the development of new drug treatments that might slow the progression of diabetic nephropathy.

Several rodent models of spontaneous diabetes (Zucker, BB rat, DB mice) exist that exhibit thickening of basement membranes and mild diffuse focal glomerulosclerosis (Marliss, E. B., et al., *Metabolism* 32(Supp. 1):1989; Schmitz, P. G., et al., *Am. J. Physiol.* 263(32):F496-F502, 1992; Valesquez, M. T., et al., *Diabetologia* 38:31-38, 1995) that resemble some of the changes seen in the kidneys of patients with diabetes. However, these models, unlike human diabetic nephropathy, do not exhibit glomerular hypertrophy, expansion of mesangial matrix leading first to focal glomerular sclerosis and proteinuria and later progressing to the development of severe global glomerulosclerosis and proteinuria with nodule formation (Kimmelstiel-Wilson lesions) followed by end stage renal disease characterized by elevations in blood urea nitrogen level and plasma creatinine concentration followed by death.

It is well recognized that strain differences may account for differences in the severity of diabetes-associated renal injury in some mouse models (Zheng, F., et al., *Kidney Inter.* 54:1999-2007, 1998). Thus, it is possible that there may be factors that predispose certain strains of rats and mice to develop diabetic nephropathy that have not yet been characterized since they exist in a genetic background which does not develop diabetes.

One such strain of a spontaneously diabetic rat that may harbor genetic factors predisposing them to renal disease is the GK rat. This strain is a non-obese, normotensive model of non-insulin-dependent diabetes mellitus (NIDDM). GK rats display glucose intolerance as early as two weeks of age (high basal serum insulin levels) and exhibit elevated plasma glucose levels following administration of a glucose load by four weeks of age (Portha, B., et al., *Diabetes* 40:486-491, 1991; Ostenson, C. G., et al., *Diabetologia* 36:3-8, 1993; Guenifi, A., et al., *Pancreas* 10:148-153, 1995). By 12 weeks of age, GK rats exhibit frank Type II diabetes characterized by elevated by fasting glucose and insulin levels and a prolonged elevation in plasma glucose levels following an oral glucose load. Several investigators have reported that GK rats exhibit some of the common histological changes in the kidney seen in most animal models of diabetes, including thickening of the glomerular basement membranes, mild expansion of the mesangial matrix, glomerular hypertrophy and mild diffuse focal glomerulosclerosis (Yagihashi, S., et al., *Diabetologia* 15:309-312, 1978; Phillips, A. O., *J. Am. Soc. Nephrol.* 9:639A, 1998). Nevertheless, extensive follow-up studies of GK rats indicate that even very old GK rats do not exhibit progressive renal disease characterized by the development of severe global glomerulosclerosis and nodule formation, marked proteinuria, and end stage renal disease (elevated BUN and plasma creatinine concentration) (Phillips, A. O., et al., *Am. J. Kidney Dis.* 37(2):400-410, 2001; Riley, S. G., et al., *J. Labor. Clin. Med.* 134(3):304-312, 1999).

An improved animal model of diabetic nephropathy is sorely needed to study the genetic basis of diabetic nephropathy, to identify new biomarkers and diagnostic tests for susceptibility to develop diabetes-related disorders and to develop new drugs and genetic therapies (siRNA, oligonucleotides, viral constructs, and/or antibody therapies) that might alter the progression of diabetes or diabetic nephropathy.

SUMMARY OF THE INVENTION

We introduced the mitochondrial genome and six loci on chromosomes 2, 11, 16, 19 and the X chromosome at markers D2Rat12, D11Rat93, D16Rat15, D19Rat 59, DXMit4 and DXMit42 of the Fawn Hooded rat, which develops renal disease but not diabetes, into the genetic background of GK rats, which have type II diabetes but do not develop progressive renal disease with nodule formation, using a backcross breeding strategy and whole genome wide genetic marker assisted selection to create a new rat strain. This strain is a type II diabetic nephropathy mimic (T2DN mimic) that develops Type II diabetes and progressive diabetic nephropathy leading to end stage renal disease.

The T2DN mimic and $GK_{FL}$ rats were extensively genotyped to confirm the regions of the genome that are different between these two strains. (A $GK_{Sweden}$ rat was used to develop our exemplary strain, but $GK_{FL}$ were chosen for comparison instead of $GK_{Sweden}$ because the $GK_{FL}$ rats were more readily available and perceived to be essentially genetically identical to $GK_{Sweden}$ rats.) This genotype information along with a detailed description of the breeding strategy will allow anyone of skill in the art to fully recapitulate and create T2DN mimic rats from GK and FHH rats as we described.

We also extensively characterized and compared the time course of the development of diabetes, histological damage in the kidney and the development of proteinuria and diabetic nephropathy in the T2DN mimic versus $GK_{FL}$ rats. The results prove that T2DN mimic rats develop progressive proteinuria, diabetic nephropathy and histological damage in the kidney (global glomerulosclerosis with nodular glomerular lesions), whereas $GK_{FL}$ rats that exhibit a similar degree of diabetes in a non-permissive genetic background do not develop diabetic nephropathy or end stage renal disease even at an advanced age (22 months old, equivalent to 70 year old man).

One embodiment of the present invention is a T2DN mimic rat or a population of rats comprising at least two T2DN mimic rats. The present invention is also a T2DN mimic rat, wherein the rat has been genetically altered such that the rat has additional genetic material or lacks genetic material from the original GK rat strains that are diabetic but do not develop diabetic nephropathy. The invention is also a rat obtained by breeding a T2DN mimic rat to a second non-diabetic rat strain. The invention is also cell lines derived from a T2DN mimic rat.

In another embodiment, the invention is a method of evaluating a test compound's effect on diabetes and diabetic nephropathy comprising the steps of (a) exposing the test compound to a T2DN mimic rat, wherein the rat would develop progressive proteinuria and glomerulosclerosis leading to diabetic nephropathy in the absence of the test compound, and (b) comparing the rat's development of diabetes and diabetic nephropathy with that seen in a control T2DN mimic rat that has not been exposed to the test compound.

Other embodiments of the invention will be apparent to one of skill in the art after review of the specification, claims, and drawings.

DESCRIPTION OF THE SEVERAL VIEWS OF THE DRAWINGS

The patent or application file contains at least one drawing executed in color. Copies of this patent or patent application publication with color drawings will be provided by the Office upon request and payment of the necessary fee.

FIG. 2A through D: Changes in plasma glucose concentration following an intraperitoneal glucose challenge (IPGTT). FIG. 2E: Progression of the area under the IPGTT curve. *=Different from age-matched GKFL. ($p<0.05$).

FIG. 5 illustrates the renal histological lesions that develop in T2DN mimic rats. Glomerular diameter is significantly larger in T2DN mimic rats (FIG. 5B) than in age matched 12 month old, non-diabetic BN control rats (FIG. 5A). Prominent thickening of glomerular and tubular basement membranes is observed at the light microscopy in 18 month old T2DN mimic rats (FIG. 5C and D, respectively). These changes are not seen in control BN rats. The earliest glomerular lesions observed at 6 months of age in T2DN mimic rats is focal segmental sclerosis (FIG. 5E). The expansion of the mesangial matrix continues to progress until the T2DN mimic rats exhibit severe global glomerulosclerosis with obliteration of nearly all capillaries in most glomeruli throughout the kidney by the time the rats are 18 months old (FIG. 5F).

FIG. 6 illustrates the development of nodular glomerulosclerosis in 18 month old T2DN mimic rats. Three glomeruli displaying extensive expansion of the mesangial matrix and the formation of acellular nodules (thin arrows) are shown (FIG. 6A-C). D-Hyaline deposition in surrounding renal arterioles is also present at this age (thick arrows).

FIG. 7 illustrates a high power view of a Kimmelsteil-Wilson lesion in a glomerulus of a 18 month old T2DN mimic rat.

FIG. 8 illustrates the lack of severe glomerulosclerosis in the kidney of 22 month old $GK_{FL}$ rats. These rats exhibit thickening of basement membranes and glomerular hypertrophy but only a mild degree of mesangial matrix expansion and glomerulosclerosis.

FIG. 11 presents a comparison of serum lipid profiles between T2DN mimic $GK_{FL}$ and BN rats. Serum cholesterol (A) and triglyceride concentrations (B) in 12 month old BN (n=10), $GK_{FL}$ (n=6) and male T2DN mimic (n=32) rats are presented. *=Different from BN. #=Different from $GK_{FL}$. ($p<0.05$).

FIG. 11A.—Linear regression of proteinuria and serum cholesterol levels (n=44). FIG. 11B.—Linear regression of proteinuria and serum triglyceride levels (n=44). (p<0.05).

DESCRIPTION OF THE INVENTION

General

Figure 1:
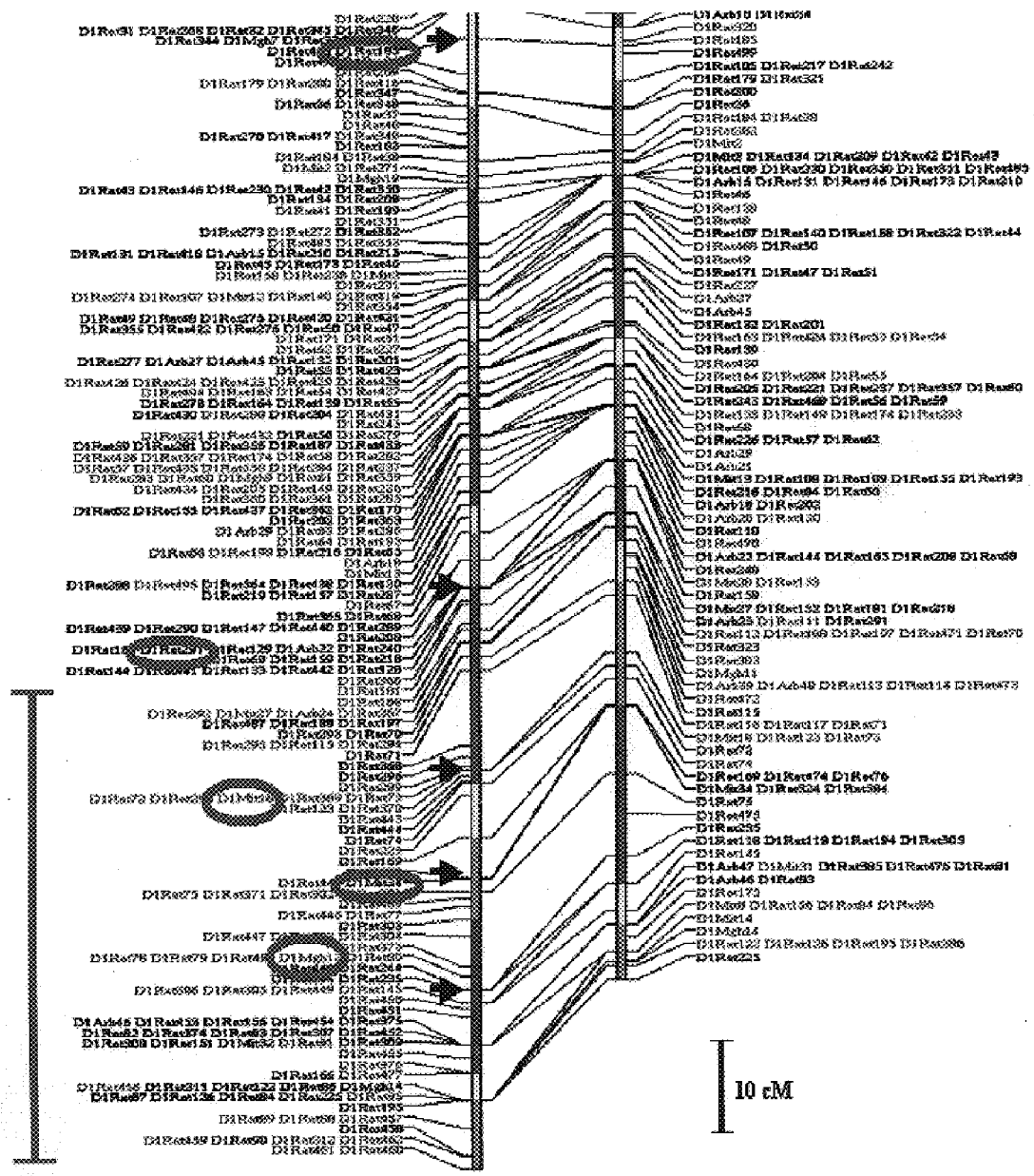
FIG. 1 is a schematic diagram of the rat chromosome 1. The microsatellite markers present in the region are displayed. Five microsatellites that were identified as being polymorphic between T2DN mimic and $GK_{FL}$ rats are highlighted in ellipses, and the black arrows indicate the individual chromosomal projections of each marker. This genomic interval that has previously been linked to the noninsulin-dependent diabetes mellitus (type II) in $GK_{FL}$ rats is also highlighted (Galli, J., et al., *Nat. Genet.* 12:31-37, 1996; Gauguier, D., et al., *Nat. Genet.* 12:38-43, 1996).

The lack of an appropriate animal model that spontaneously develops diabetic nephropathy has severely hindered the search for drugs that can prevent progressive renal disease in diabetes and the genes underlying this disease. The present invention supplies an animal model of diabetic nephropathy that spontaneously develops type II diabetes, progressive proteinuria leading to end stage renal disease and death. This animal, which we have named "T2DN mimic" for "type II diabetes nephropathy mimic" is a suitable animal model for the study of diabetic nephropathy and to develop drugs to treat and prevent this condition.

To characterize our model system, the Examples below contrast the development of diabetes and renal damage in two strains of rats with type II diabetes, i.e., T2DN mimic and $GK_{FL}$ rats, which express identical alleles at 97% of 543 microsatellite markers assayed across the genome. The time course and severity of the development of insulin resistance and diabetes is similar in T2DN mimic and GKFL rats. However, T2DN mimic rats develop overt proteinuria by 6 months of age, which progresses with time and leads first to the expansion of the mesangial matrix and the development of focal glomerulosclerosis, thickening of basement membranes, vascular hylanosis and, eventually, severe global nodular glomerulosclerosis, end stage renal disease and death.

As described above, the changes in the histology of the kidney of T2DN mimic rats closely mimic those seen in the kidney of diabetic patients. In contrast, diabetic GKFL rats exhibit much less proteinuria, thickening of basement membranes and only a slight degree of glomerulosclerosis. However, the degree of renal disease and glomerulosclerosis does not progress over the 22 months length of the study and these rats never develop nodular glomerulosclerosis and end stage renal disease like T2DN mimic rats. This comparison indicates that the T2DN rat is a suitable model for type II diabetic nephropathy, and while the $GK_{FL}$ can serve as closely genetic related diabetic control strain that does not develop progressive renal disease. The availability of this control strain allows one to dissect the influence of diabetes and other metabolic factors versus genetic susceptibility in the development of diabetic nephropathy.

The T2DN Mimic Rat

In one embodiment, the present invention is a rat model of diabetic nephropathy that develops progressive glomurulosclerosis and proteinuria leading to end stage renal disease and renal Kimmelsteil-Wilson lesions like those seen in patients with diabetic nephropathy. We refer to this rat as a "T2DN mimic" rat. The rat is also characterized by having the mitochondrial genome and six loci on chromosomes 2, 11, 16, 19 and the X chromosome at markers D2Rat12, D11Rat 93, D16Rat15, D19Rat 59, DXMit4, and DXMit42 of the Fawn Hooded rat on the $GK_{Sweden}$ genetic background.

The rat model develops overt proteinuria, focal glomerulosclerosis, expansion of mesangial matrix of the glomerulus, thickening of renal basement membranes, vascular hylanosis and nodular glomerulosclerosis, as described below in the Examples.

One may obtain the T2DN mimic rat by following the breeding program described below in the Examples. We have described below in the Examples a method of creating the T2DN mimic rat by cross-breeding of a male $GK_{Sweden}$ rat with a female FHH/EurMcw (FHH) rat. One may obtain the $GK_{Sweden}$ rat from the Karolinska Institute, Sweden. One may obtain the FHH/EurMcw rat from Charles River Laboratories, Wilmington, Mass., from Erasmus University, Rottendam, Netherlands, or from the Medical College of Wisconsin, Milwaukee, Wis.

We believe that one could also obtain the T2DN mimic rat by breeding other GK strains, such as $GK_{FL}$ or GK rats sold by Charles River Laboratories, with other FHH strains. One would need first to confirm that the allele sizes of the important FHH loci were the same as those that we report for FHH/EurMcw-rats and that the genetic background and that the characteristics of the GK strain chosen were similar to those described above. GK rats, in general, may be obtained from Karolinska Institute in Sweden, and FHH rats, in general, may be obtained from Medical College of Wisconsin, Erasmus University or Charles River Laboratories.

Alternatively, a breeding colony of T2DN mimic rats consisting of at least 20 mating pairs is maintained by the Inventors at the Medical College of Wisconsin, Milwaukee, Wis. and a separate breeding colony of a minimum of 30 breeding pairs is available for purchase and is maintained by PhysioGenix Inc. at its animal care facilities in the Wood Memorial VA Hospital, Milwaukee, Wisc. A third commercial breeding colony of a minimum of 15 breeding pairs is maintained by PhysioGenix in barrier isolators at Charles River Laboratories in Wilmington, Mass. In aggregate these colonies of T2DN mimic rats produce a minimum of 100 rats per month which are available for sale and to maintain the 3 breeding colonies.

In another embodiment, the present invention is a T2DN rat with genetic modifications relative to the rat referenced in the paragraph above. These genetically modified T2DN mimic rats may have genetic deletions or additions or other uncharacterized genetic modifications. One would obtain such a rat by using genetic modification protocols known to the art applied to a T2DN mimic rat. Specific examples of how to create such genetically modified T2DN mimic rats are described below.

For example, useful genetic modifications of T2DN mimic would include:

1. Use the T2DN mimic rat in F2 cross with diabetic resistant rat or the diabetic nephropathy resistant $GK_{FL}$ rat to perform genetic mapping studies to positionally clone the region of the genome containing the genes that underlie diabetes, diabetic nephropathy, diabetic induced eye disease (retinopathy), diabetic neuropathies and/or vascular and cardiac end-organ damage associated with diabetes.

2. Develop congenic substrains of T2DN mimic rats from the F2 population by backcrossing the F2 rats with crossovers in the quantitative train loci with T2DN mimic rats for 6-10 generations to isolate small region of the genome that cures or increases diabetes, diabetic nephropathy, and the eye, cardiac and vascular end-organ damage in T2DN mimic genetic background. The description of how to create a congenic substrain of T2DN mimic is found above.

The general method consists of taking T2DN mimic rats and breeding them with a diabetic resistant strain, such as Brown Norway (BN) rat. The F1 rats are intercrossed yielding an F2 population that is genotyped. Rats with BN genes in the regions of the genome that are linked with resistance to diabetes, diabetic nephropathy and cardiac and vascular injury that were identified in a genetic mapping studies described below, will be backcross bred to other T2DN mimic rats. The pups will be genotyped and rats that remain heterozygous for the region of interest will be selected and backcross bred with T2DN mimic rats for another generation. This process will be repeated for 5-6 generations until one obtains rats that are heterozygous for the regions of interest but are homozygous for T2DN mimic genes at all other regions of the genome. At this point the rats will be mated to produce rats that are homozygous for the BN or other resistant genes over the selected region and homozygous for T2DN mimic genes throughout the rest of the genome. The original T2DN mimic rats would serve as the disease-susceptible rats.

The rats would be phenotyped for diabetes by measuring plasma glucose levels following a 24 hour fast and for type II diabetes by measuring the insulin levels and plasma glucose levels following an intraperitoneal administration of glucose.

The rats would be phenotyped for diabetic nephropathy by collecting urine and measuring urinary excretion of protein and plasma creatinine concentrations at various times, 12, 18 and 22 months of age. When there was a significant difference between the congenic rats and the T2DN mimic controls, the rats would be sacrificed and the kidneys prepared for histological evaluation of the degree of glomerular disease and renal damage.

Diabetic-induced vascular dysfunction would be assessed by removing the aorta from rats and studying vascular responses to vasoconstrictors, norepinephrine and vasospressin and vasodilators, acetylcholine and DEA nonoate, a nitric oxide donor, as we have previously described (Yu, et al., *J. Hypertension* 21:1125-1135, 2003).

Diabetic induced cardiac dysfunction would be evaluated by weighing the heart to assess the degree of cardiac hypertrophy. In addition, the heart will be histologically prepared and sections evaluated to measure the area of the wall of the left ventricle and to determine the degree of fibrosis of the ventricular wall as previously described in Yu, et al., 2003.

These congenic substrains will narrow the region around the gene of interest to <50 genes. The curative gene can then be identified using cDNA and/or oligonucleotide expression arrays looking for a differentially expressed gene between the congenic (resistant) and T2DN mimic (susceptible) strains that are nearly genetically identical (>99% similar). The mutation in the gene of interest would be confirmed by direct sequencing of the genes isolated from the DNA of the congenic and T2DN mimic strains.

These identified resistance or susceptibility genes could be further developed as a diagnostic test to identify diabetic patients at risk to develop renal, cardiac, vascular or eye damage. The gene could also be used as a drug target to screen chemical libraries to find compounds (drugs) that normalize the expression of the gene of interest in cells cultured from the congenic and T2DN mimic strain. These compounds will be useful to treat patients.

Therapeutic agents (small molecules or biologicals) could also be developed against the gene of interest identified in the congenic strain using antisense oligonucleotides, small interfering RNAs, viral constructs, gene therapy aimed at normalizing the expression of the targeted gene in the T2DN mimic strain.

3. Use the T2DN mimic rat in an ENU mutagenesis or gene trap strategies recently described in rats (Zan, et al., *Nat. Biotechnology* 21:645-651, 2003) and in common practice in mice (Soewato, et al., *Method Mol. Biol.* 209:249-266, 2003; Baier, *Phys. Genomics* 14:111-113, 2002; Cox and Brown, *Curr. Opin. Genet. Dev.* 13:278-283, 2003) to knockout specific genes to create mutants that are resistant to the development of diabetes, diabetic nephropathy, and/or cardiac, vascular, nerve and eye damage (diabetic neuropathy and retinopathy) associated with diabetes. Alternately, one can randomly knockout genes in the T2DN mimic strain using ENU mutagenesis and screen the mutants for a change in phenotype to identified mutations in genes (drug targets) that can reverse clinic course of disease in T2DN mimic rats.

T2DN mimic rats can be included as one of the strains in a recombinant panel (see U.S. Ser. No. 10/379,217) to determine the genetic basis of drug or toxin responses or the influence of diabetes and genetic susceptibility to diabetic nephropathy or any other phenotype of interest (drug or toxin responses, response of heart, kidney, vasculature or eye to develop endorgan damage following surgical, environmental or chemical challenges).

In another embodiment, the present invention is a rat obtained by mating of the T2DN rat with a rat of any other rat strain to create new strains with unique disease phenotypes.

For example, the T2DN mimic rat can be mated with other inbred rat strains with other specific disease traits such as Dahl salt-sensitive or spontaneously hypertensive rats SHR (hypertension), Zucker rats (dislipedimia and obesity), BB rats (type I diabetes) or the 44 strains of Dahl or Fawn Hooded X Brown Norway consomic lines available at Medical College of Wisconsin (pga.mcw.edu) or Charles River Laboratories (Wilmington, Mass.) (in which over 300 different cardiovascular and metabolic trains have been characterized) to create new and unique complex animal models of human disease such as Syndrome X, characterized by hypertension, obesity, type II diabetes, dislipidemia and cardiovascular disease.

Examining Test Compounds

In another embodiment, the present invention is a method of examining test compounds for potential effect on diabetic nephropathy. The method would typically comprise the step of exposing the T2DN mimic rat to a test compound and then examining the development of diabetic nephropathy as compared to a control T2DN rat that has not been exposed to the compound.

A typical protocol for this evaluation would be as follows:

Experiments will typically be performed on 9-12 month old male T2DN mimic rats. Male rats will be studied because the severity of diabetic nephropathy is greater in male versus female rats. The rats will be uninephrectomized and fed a purified diet containing 60% sucrose which increase the degree of diabetes and together with the uninephectomy accelerates the development of diabetic-induced renal disease.

After a 1 week equilibration period, blood and urine samples will be collected to measure baseline fasting glucose and lipid levels, plasma creatinine concentration and protein and albumin excretion.

Rats (8-10 per group) will randomly be assigned to 4 treatment groups and treated orally by gavage or ip or iv injections of a low, medium or high dose of the test compound or vehicle. Drugs will be given once or twice a day dependent on their half-lives.

Typical classes of known compounds that one might test to prevent diabetic-induced nephropathy include: angiotensin II receptor antagonists, converting enzyme inhibitors, TGF beta antagonists and antibodies, growth factor inhibitors, PPar receptor agonists, antihypertensive agents, insulin sensitizing drugs, etc.

The mid-range dose would be chosen based on pharmacokinetic information and the known effective dose (ED50). The high dose would typically be 5-10 times greater and the low dose would typically be 5 times lower than the mid-range dose.

The rats would typically be treated for 4, 8 or 12 weeks. Urine and plasma samples would be collected at 2 week intervals to measure plasma creatinine concentrations (index of renal function), fasting glucose and insulin levels (indicies of diabetes), plasma cholesterol and triglyceride levels, urinary excretion of protein and albumin (indices of renal damage). At the end of the experiment the rats will be sacrificed with pentobarbital, a sample of blood will be collected for clinical chemistry and the kidney and heart collected, weighed (to measure hypertrophy), fixed in formalin. The samples will be sectioned and stained with Mason Trichrome stain which stains fibrotic tissue (collagen and fibronectin) blue. The diameter of the glomeruli will be measured and the percentage of the glomerular area filled in with mesangial matrix will be scored on at least 30 glomeruli per section using an image analysis program.

One would also measure the percentage of renal area stained blue (interstitial fibrosis) and stained red (protein casts in renal tubules). The degree of proteinura, albuminuria and glomerulsclerosis as well as plasma creatinine concentrations and the percentages of renal fibrosis and necrosis will be compared in the drug treated and vehicle control groups. The significance of differences in mean values between treatment groups will be determined by an analysis of variance followed by a Student Newman's Kuels Post Hoc test. One would expect to find a dose related reduction in plasma creatinine concentration, urine protein and albumin excretion and the percentage of glomular capillary area filled in with matrix material for drugs that are effective in reducing the progression of glomerulosclerosis.

Another embodiment of the present invention is a method of examining test compounds for potential effect on cardiac, vascular and eye damage produced by type II diabetes. Previous investigators have reported that GK rat is a useful model to determine the cardiac, vascular and eye damage produced by type II diabetes. Since the T2DN mimic rats shares 97% of its genome with GK rats and develops similar degree of diabetes and glucose intolerance it too should be useful to study the effects of test compounds to reduce vascular, cardiac and eye complications and end organ damage associated with type II diabetes.

In a typical experiment, 6 week old T2DN mimic rats would be treated with various doses of a test compound or vehicle for 12 to 18 weeks. The test compounds could be given orally (by gavage or in the drinking water) or by iv or ip injections on a daily basis. At the end of 12 to 18 weeks of treatment the heart would be weighed (to access the degree of hypertrophy) and histologically sectioned and stained with Mason's trichrome stain. The area of the left ventricular wall would be measured using a computerized morphometric program and the degree of fibrosis of the left ventricular wall and perivascular fibrosis assessed by measuring the area of the tissue stained blue (for collagen and fibronectin) as we have previously described in (Yu, et al., *J. Hypertension* 21:1125-1135, 2003). We expect to find that test compounds that are effective at reducing diabetic induced cardiac damage would result in a lower hearth weight, thinner ventricular wall and less fibrosis of the left ventricle.

Diabetes also results in endothelial dysfunction, characterized by a reduced response to endothelial dependent vasodilators that release nitric oxide. Diabetic induced vascular dysfunction would be assessed by removing the aorta from control T2DN mimic and rats treated with test compounds and mounting vascular rings in a myograph in vitro as we have previously described Yu, et al., 2003. The responses of the aorta to cumulative addition of vasoconstructors, norepinephrine and vasospressin (10-9 to 10-5 M) and vasodilators, acetylcholine and DEA nonate (10-9 to 10-3 M) will be determined as we have previously described (Yu, et al., supra, 2003). Compounds that would be effective in the treatment of diabetic-induced vascular dysfunction leading to impotence, vascular insufficiency (anything from leg cramps to necrosis and limb amputation) would improve endothelial dysfunction and restore the vasodilator responses to acetylcholine and bradykinin in T2DN mimic rats with long standing diabetes.

Determination of Genetic Elements

In another example of the present invention, one might wish to compare the genome of T2DN mimic rats (disease susceptible) with GKFL rats (closely related resistant rats) or other diabetic resistant strains, such as BN rats, to determine what genetic elements might be responsible for development of diabetic nephropathy.

For example, one might mate a male T2DN mimic rat (diabetic nephropathy susceptible) with a female Brown Norway (diabetic nephropathy resistant) rat to create a F1 hybrid population. Male and Female rats in the F1 would be mated to create several hundred (3-500) F2 offspring. These rats would be uninephrectomized and fed a 60% sucrose diet. Urine and plasma samples will be collected at 6, 12 and 18 months of age for measurement of proteinuria, albuminuria and plasma creatinine concentration. The kidneys will be collected, sectioned and scored for the degree of glomerulosclerosis. The rats will be genotyped using 500 markers equally spaced throughout the genome. Linkage analysis of the renal disease phenotypes will be performed with the genotypes for all rats using Mapmaker program (Lander and Kruglyak, *Nat. Genet.* 11:241-247, 1995).

EXAMPLES

Materials and Methods

Generation of the T2DN Mimic Strain

The T2DN mimic strain can be created by introducing the mitochondrial genome and loci on chromosomes 2(D2Rat12), 11 (D11Rat93), 16 (D16Rat15), 19 (D19Rat59), X (DXMit4) and (DXMit42) of Fawn Hooded rats (FHH/EurMcw) that develop renal disease but are not diabetic into the genetic background of a $GK_{Sweden}$ strain of rats that develop Type II diabetes but not renal disease. We bred a male $GK_{Sweden}$ rat obtained from the Karolinska Institute, Sweden with a female FHH/EurMcw rat (Medical College of Wisconsin) to produce an $F_1$ generation with 1 copy of FHH and 1 copy of $GK_{Sweden}$ at all autosomal genes and the mitochondrial genome of FHH rats. Female $F_1$ rats were backcrossed with a male $GK_{Sweden}$ rat to create an N2 generation. Female N2 rats with the most $GK_{Sweden}$ alleles across the genome and which are heterozygous for D11Rat93, D16Rat15, D19Rat59, D2Rat12, DXMit4 and DXMit42 were selected using whole genome marker assisted selected strategy to be backcrossed with a male $GK_{Sweden}$ rat to create an N3 generation. This process was repeated for 5 additional backcross generations. Thereafter, male and female rats of the N6 generation were intercrossed to create the T2DN mimic strain.

Genetic selection in each generation of backcross breeding was done by extracting DNA from females, and each rat was genotyped by PCR at 180 microsatellite markers, polymorphic between $GK_{Sweden}$ and FHH, along the 20 autosomes and the X chromosome. The percentage of $GK_{Sweden}$ alleles retained in each rat was determined and females that carried the most $GK_{Sweden}$ alleles (2 S.D.) were subsequently chosen to be backcrossed with a male $GK_{Sweden}$ rat. This breeding strategy allowed for the fast fixation of most of the original $GK_{Sweden}$ genome, except for the mitochondrial DNA, which was inherited from the female FHH rat used in the first intercross and retained the six markers from FHH that are noted in the above description.

The present phenotyping studies were done on rats obtained in the 9-12 generation of rats following the first $GK_{Sweden}$-FHH intercross. By "T2DN mimic strain" we mean the inbred strain of rats with the mitochondrial genome of FHH and the additional alleles described above and below in a largely fixed genetic background of GK rats. We refer to the particular strain of T2DN mimic rats developed in our laboratory as T2DN $mimic_{MCW}$.

Genetic Comparison of the T2DN $Mimic_{MCW}$ and $GK_{FL}$ Rats

To determine the degree of genetic relatedness between T2DN mimic and $GK_{FL}$ rats (purchased from Dr. Robert V. Farese, at the VA Medical Center in Tampa, Fla.), as well as to assess the degree of the FHH genome retained in the T2DN mimic strain, a genome-wide scan with 543 microsatellite markers equally spaced along the genome was carried out. The markers selected were polymorphic between $GK_{FL}$, FHH rats and exhibited a high degree of polymorphism among the 47 rat strains characterized in our previous studies (Steen, et al., Genome Res. 9: 1-8, 1999) to maximize the likelihood of detection of polymorphism between the GK strains.

Genotyping

DNA was extracted from a 1 mm section of tail that was incubated in 500 µL lysis buffer containing (100 mM Tris HCl pH 8.5, 5 mM EDTA, 0.2% SDS, 200 mM NaCl, 50 µg Proteinase K) overnight at 55° C., followed by an isopropanol precipitation and resuspension in TE buffer (10 mM Tris HCl pH 7.4, 0.1 mM EDTA). The DNA was diluted to a final concentration of 5 ng/µL. The rats were genotyped using PCR. Prior to PCR, the primers were radiolabelled with $^{32}P$-γ-ATP, using T4 polynucleotide inase (NEB, Beverly, Mass.). PCR was carried out as previously described (Jacob, H. J., et al., Nat. Gene. 9:63-69, 1995) and the products were electrophoretically separated in 6% polyacrylamide gels.

Characterization of T2DN Mimic Diabetes and Glucose Intolerance

Male T2DN $mimic_{MCW}$, $GK_{FL}$ and BN rats were subjected to an intraperitoneal glucose tolerance test (IPGTT), at 3, 6, 9, and 12 months of age. Following the determination of fasting (12 hours) glucose levels, the animals were injected with 1 g/Kg of a 2.8 M glucose solution, intraperitoneally. 10 µL blood samples were then drawn via a tail incision at 30, 60, 90, and 120 minutes following administration of the glucose load and plasma glucose levels were measured using reagent strips that were read in a glucose meter (Bayer Corp., Elkhart, Ind.).

Proteinuria

T2DN $mimic_{MCW}$, $GK_{FL}$ and BN rats were placed in metabolic cages at 1, 3, 6, 9, 12, and 18 months of age and urine was collected for 24 hours. Total protein concentration in the urine was determined calorimetrically using the Bradford method (BioRad, Hercules Calif.) (Bradford, D. M., Anal. Biochem. 72:248-254, 1976).

Determination of Lipid Profiles

Serum cholesterol and triglyceride concentrations were compared in T2DN mimic and $GK_{FL}$ rats at 3, 6, 9, and 12 months of age. For this procedure, the rats were fasted overnight and 500-700 µL of blood was collected from the tail vein. Total cholesterol and triglycerides were determined using kits from Sigma Diagnostics, St. Louis, Mo.

Histology

Renal histology was assessed in T2DN $mimic_{MCW}$, $GK_{FL}$ and BN rats sacrificed at 1, 6, 12, 18 and 22-24 months of age. The right kidney was removed and weighed and then fixed in 10% formalin solution followed by embedding in paraffin. Two 4 µm thick sections were prepared from each kidney and stained with Periodic Acid-Schiff (PAS) and/or Mason Trichrome stain. The sections were examined by light microscopy for the degree of vascular injury, renal interstitial fibrosis and the degree of glomerulosclerosis and expansion of the mesangial matrix in the glomerulus. Lesions in individual glomeruli were scored on a 0 to 4+ scale with 0 representing a normal glomerulus, 1+ up representing a 25% of loss of capillaries in the glomerular tuft, 2+ 50% loss, 3+ 75% loss, and 4+ representing more than 75% of the glomerular tuft sclerosed. A total of 30-35 glomeruli per kidney were analyzed, and an average score (sclerosis index) calculated. Glomerular volumes were also determined using a modification of the Maximal Planar Area method (Pagtalunan, M. E., et al., Kidney Internat. 57:2644-2649, 2000). For the digitally circumvention of the glomerular perimeter, the Metamorph Image Analysis software was applied.

RESULTS

Genotype of T2DN Mimic Rat

The T2DN mimic strain was characterized with an extensive genome-wide scan using 543 microsatellite markers. The genotype revealed six loci, on chromosomes 2 (D2Rat12), 11 (D11Rat93), 16 (D16Rat15), 19 (D19Rat59) and X (DXMit4 and DXMit42) that were still heterozygous for FHH alleles. Given the genomic interval between these and the closest microsatellite markers, we estimate that at a maximum <1% of FHH genome was retained on the autosomal chromosomes (1-20, plus X) in the T2DN mimic strain. Moreover, since a female FHH rat was used to produce the F1 rats in this cross, T2DN mimic rats still harbors the mitochondrial DNA of FHH rats. This assertion was confirmed by sequencing the mitochondrial genome of T2DN mimic and comparing it with that of GK and FHH rats.

$GK_{FL}$ Rats

A genome-wide scan was also performed to compare the same 543 polymorphic markers between the diabetic nephropathy susceptible T2DN mimic and the diabetic nephropathy resistant $GK_{FL}$ strains. The results indicate that there are 8 genetic differences across to 543 markers tested between these two strains. Three differences were present at markers D3Rat57, 11 (D11Mgh5), and 12 (D12Rat22). Five additional differences were identified on chromosome 1, at markers D1Rat291, D1Mit18, D1Mit34 and D1Mgh12 within 30 cM from each other. The fifth difference at D1Rat185 mapped 57 cM from the telomere on chromosome 1 (FIG. 1). These five markers represent at a maximum of 2% of the genome tested. Overall genotyping results indicate that the diabetic nephropathy sucsceptible T2DN mimic and diabetic nephropathy resistant $GK_{FL}$ strain are 97% identical at the microsatellite level across the entire genome.

Figure 2:
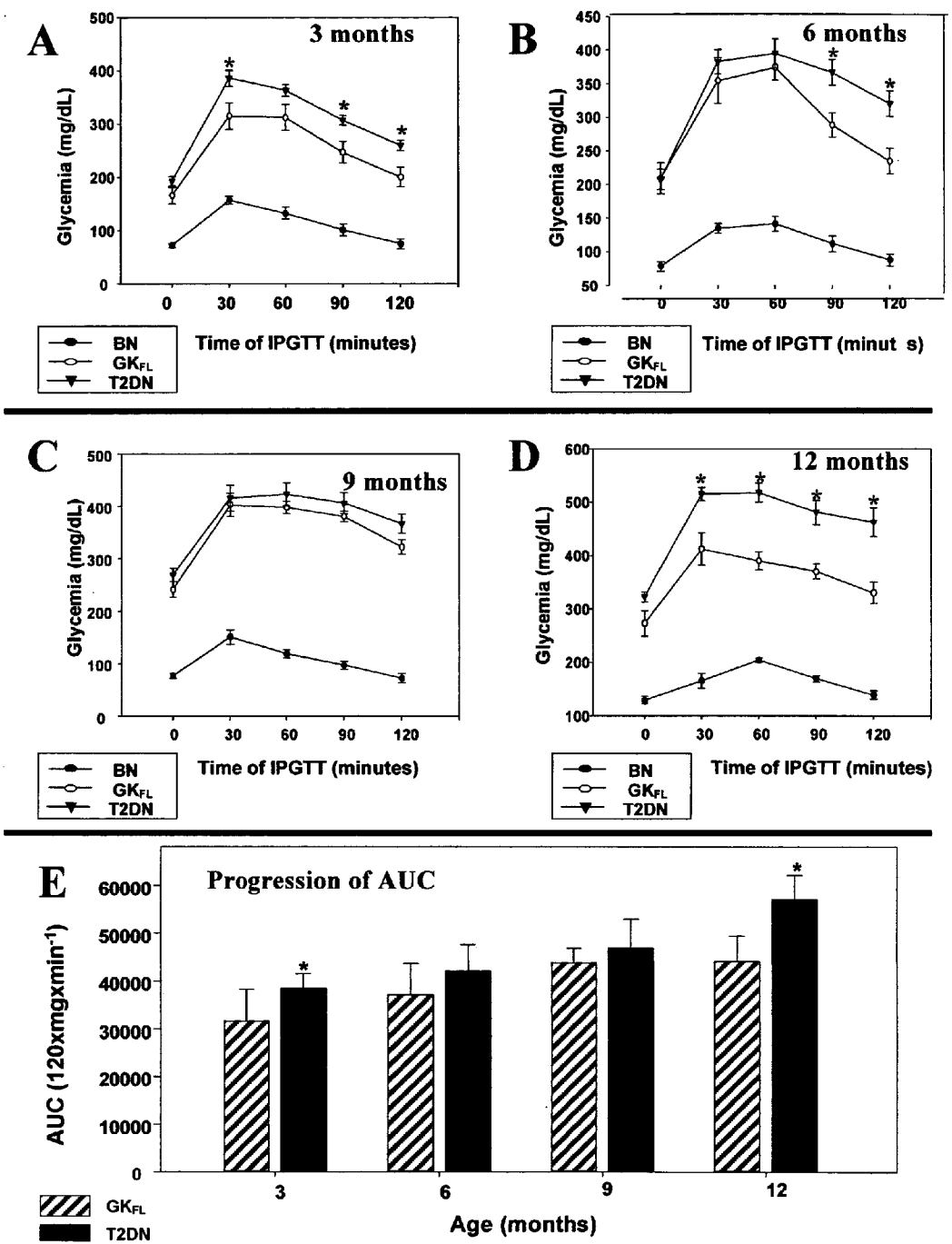
FIG. 2 presents a comparison of the development of type II diabetes in T2DN mimic and $GK_{FL}$ rats. A total of 7 animals per group were tested at all ages.

Comparison of the Development of Diabetes and Glucose Intolerance in T2DN Mimic Strain and $GK_{FL}$ Rats Baseline fasting glucose levels were elevated to >200 mg/dl and significantly above values seen in BN rats in both T2DN mimic strain and $GK_{FL}$ rats that were 6 months old (FIG. 2). However, there was no significant difference in fasting glucose levels seen in GK and T2DN mimic strain rats at any point during the study. Both $GK_{FL}$ and T2DN mimic strain exhibited glucose intolerance as indicated by the increase area of the plasma glucose clearance cure following an intraperitoneal injection of a glucose load. The degree of glucose intolerance was slightly greater in T2DN mimic strain versus $GK_{FL}$ rats at 3 months of age, but no significant difference was observed in 6 and 9 month old $GK_{FL}$ and T2DN mimic rats. After 12 months of age, the T2DN mimic rats exhibited a 20-30% greater glucose intolerance than that seen in $GK_{FL}$ rats.

Progression of Renal Disease in T2DN Mimic Strain and BKf1 Rats

Proteinuria

Figure 3:
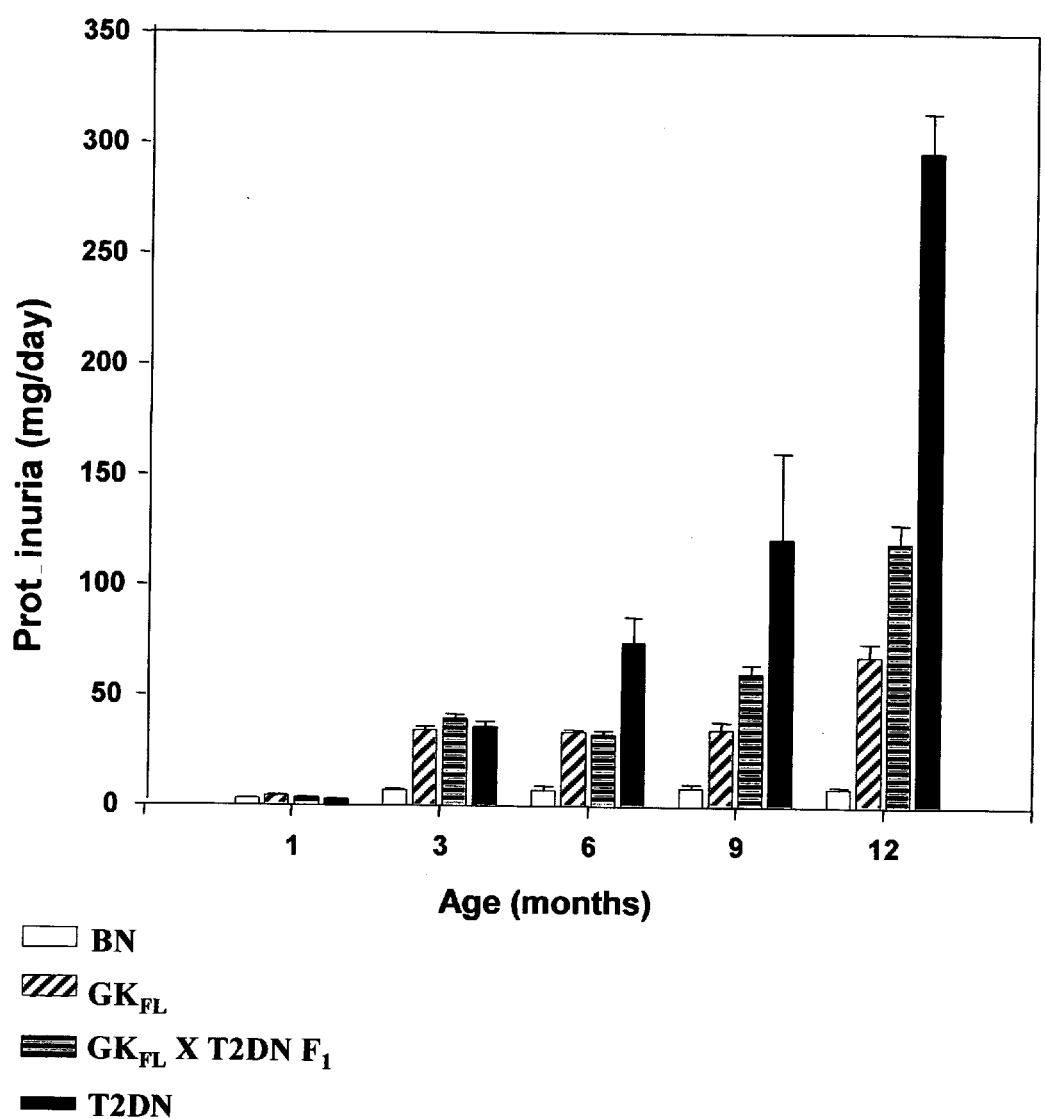
FIG. 3 compares the development of progressive proteinuria in T2DN mimic, $GK_{FL}$, and a F1 cross of T2DN mimic×$GK_{FL}$ and BN control rats. Seven animals were tested in each group. *=Different from BN rats, t=$p<0.05$. T2DN mimic versus $GK_{FL}$ rats. T2DN mimic×$GK_{FL}$ $F_1$; #=Different from $GK_{FL}$. ($p<0.05$).

A longitudinal screening of proteinuria in T2DN mimic strain rats (FIG. 3) shows that at 1 month of age, proteinuria is similar in T2DN mimic rats, $GK_{FL}$ and control Brown Norway rats (BN). Proteinuria became significantly elevated in 3 month old T2DN mimic and $GK_{FL}$ rats. The degree of proteinuria progresses with time (FIG. 3) and by proteinuria reaches 297.4±17.1 mg/day in 12 months old T2DN mimic strain. The $GK_{FL}$ rat does not develop severe proteinuria at 12 months of age. Proteinuria was also measured in a group of F1 progeny generated from a cross of T2DN mimic strain and $GK_{FL}$ rats. Similar to what was observed in BN and GKFL rats, proteinuria only became significantly elevated relative to BN rats when the F1 rats were 12 months of age and at this time it was still very low compared to that seen in the T2DN mimic rats.

Figure 4:
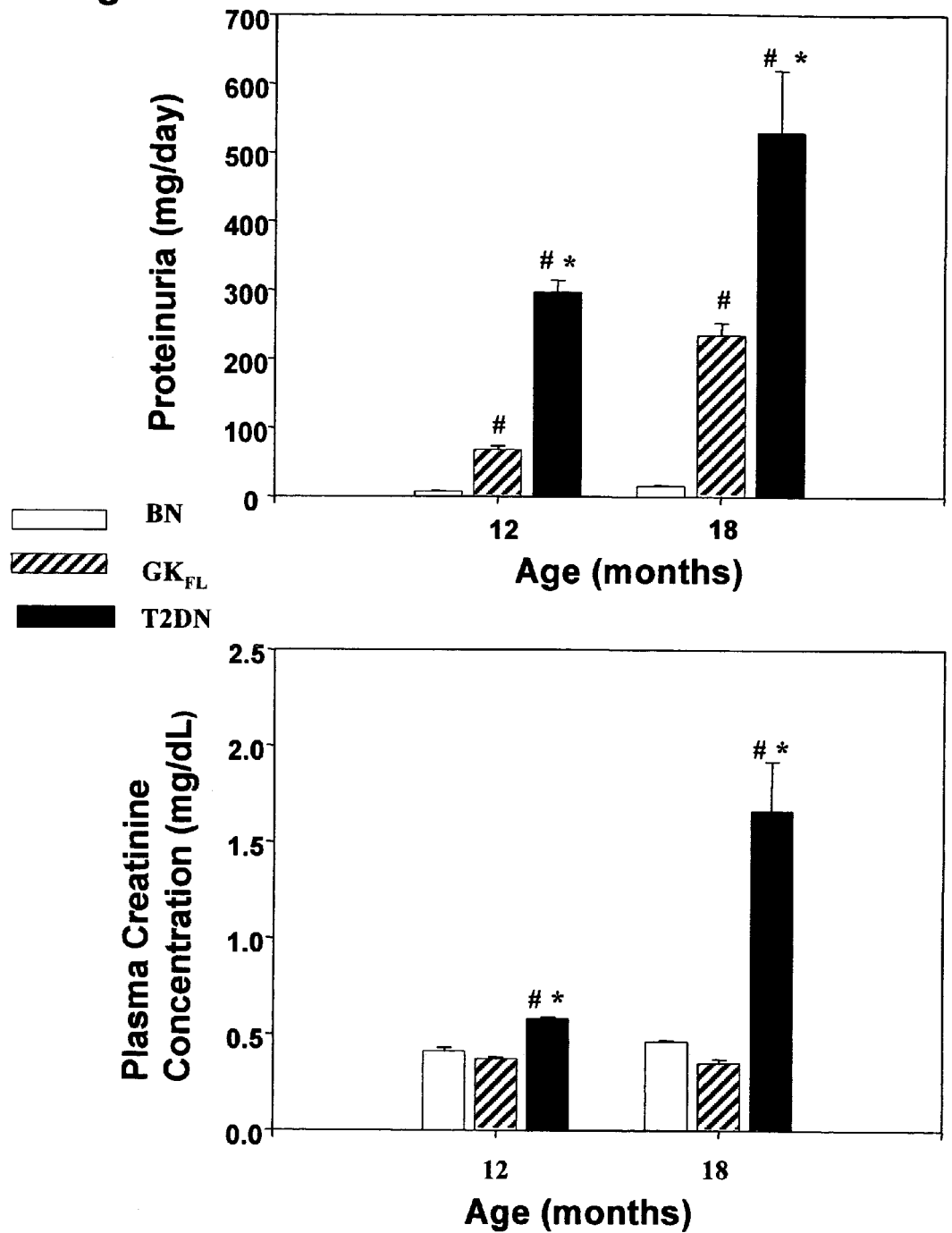
FIG. 4 compares the progression of proteinuria and changes in plasma creatinine concentration in 12 and 18 month T2DN mimic, $GK_{FL}$ and BN rats.

To determine whether T2DN mimic rats develop progressive renal disease leading to end stage renal disease we measured proteinuria and plasma creatinine concentration in 18 month of BN, $GK_{FL}$ and T2DN $mimic_{MCW}$ rats. The results are presented in FIG. 4. Serum creatinine concentration did not increase in 18 or 22 month old $GK_{FL}$ rats relative to BN rats indicating that they do not exhibit progressive renal disease leading to ESRD. In contrast, proteinuria increased from 300 to more than 500 mg/day in 12 versus 18 month old T2DN mimic rats and was significantly higher than the values seen in diabetic $GK_{FL}$ rats (FIG. 4). Moreover, plasma creatinine levels rose from 0.6±0.1 to 1.7±0.1 mg/dl in 12 versus 18 month old T2DN mimic rats, but remained in the normal range in $GK_{FL}$ rats.

Histologic Changes in the Kidney

Histological analysis of the kidneys of T2DN mimic strain revealed an extensive pattern of progressive renal disease characterized by extensive glomerular and tubular injury. As shown in FIG. 5E, the predominant form of glomerular damage at 12 months of age is glomerular hypertrophy (FIG. 5B) focal segmental glomerulosclerosis, with regional adhesion of glomerular tuft to Bowman's capsule associated with expansion of the mesangial matrix and filling in of capillaries (FIG. 5E). There is pronounced thickening of both glomerular and tubular basement membranes in the kidneys of 12 and 18 month old T2DN mimic strain rats (FIG. 5C and 5D).

At 12 months of age, glomeruli in the T2DN mimic strain also exhibit expansion of mesangial matrix and appearance of PAS positive material. This expansion of the mesangial matrix is even more prominent in T2DN mimic strain rats when they are 18 months old, with nearly complete obliteration of glomerular capillaries in nearly every glomerulus, indicative of severe global glomerulosclerosis (FIG. 5F). More importantly, in many glomeruli one can find asymmetric, acellular nodules in the glomerulus (FIGS. 6 and 7), which resemble Kimmelsteil-Wilson nodules that are characteristic of diabetic nephropathy in man.

In contrast, even at 18 or 24 months of age $GK_{FL}$ rats exhibit only a very modest degree of expansion of the mesangial matrix and focal glomerulosclerosis. The degree of injury is not greater than that associated with normal aging in BN rats. $GK_{FL}$ did not form nodular lesions in the glomerulus (FIG. 8). However, they still exhibited thickening of glomerular and proximal tubular basement membranes and hypertrophy of the glomerulus which is common change in the kidney seen in many models of diabetes that do not develop diabetic nephropathy.

Figure 9:
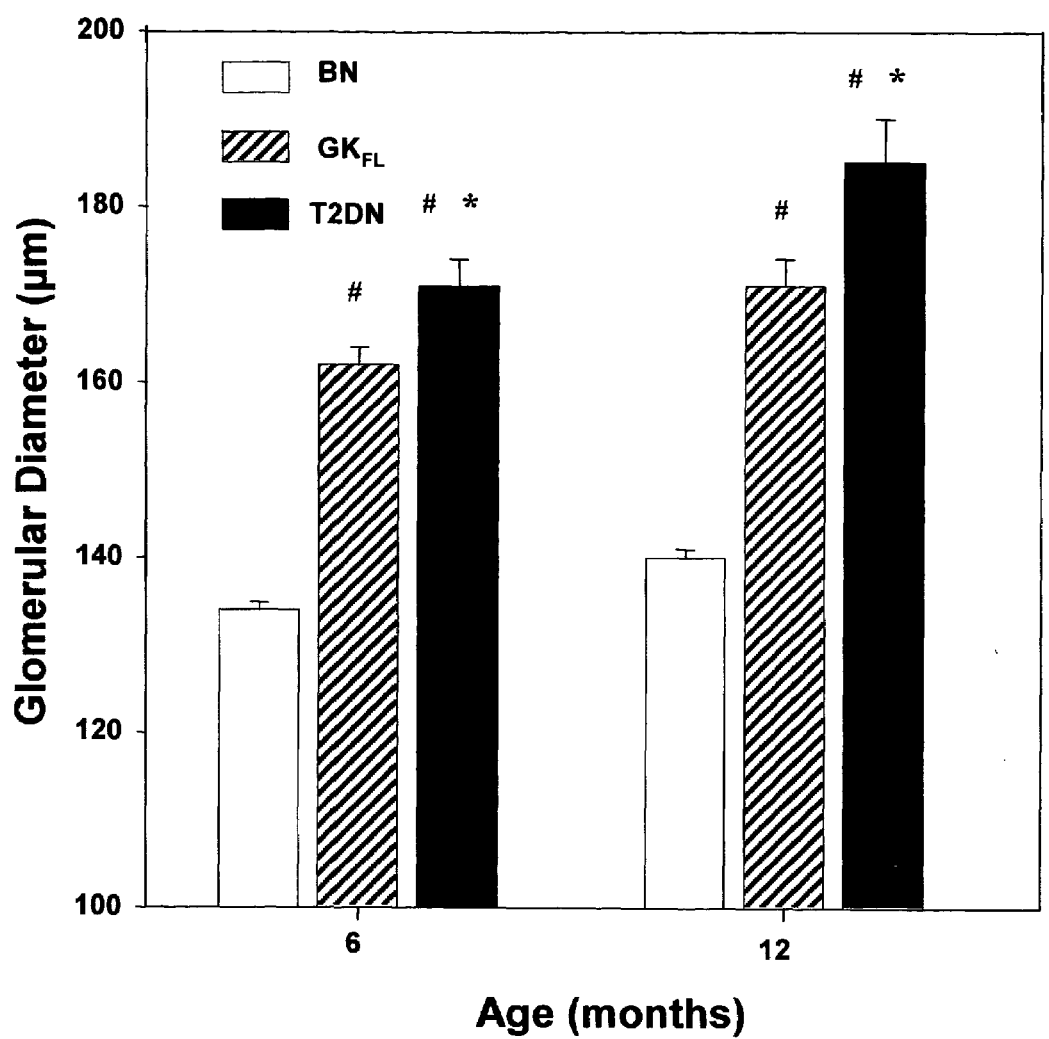
FIG. 9 presents a comparison of glomerular diameters in $GK_{FL}$, T2DN mimic and BN rats. Glomerular diameters are significantly larger in $GK_{FL}$ and T2DN mimic rats than in BN rats at 6 and 12 months of age. There is no difference in the degree of glomerular hypertrophy in the kidneys of $GK_{FL}$ and T2DN mimic rats.

A comparison of the degree of glomerular hypertrophy in T2DN mimic, $GK_{FL}$ and BN rats are presented in FIG. 9. The diameter of the glomerulus was significantly greater in 6 and 12 month old $GK_{FL}$ and T2DN mimic rats relative to BN rats. There was no significant difference in the size of the glomerulus in $GK_{FL}$ and T2DN mimic rats at any age.

Figure 10:
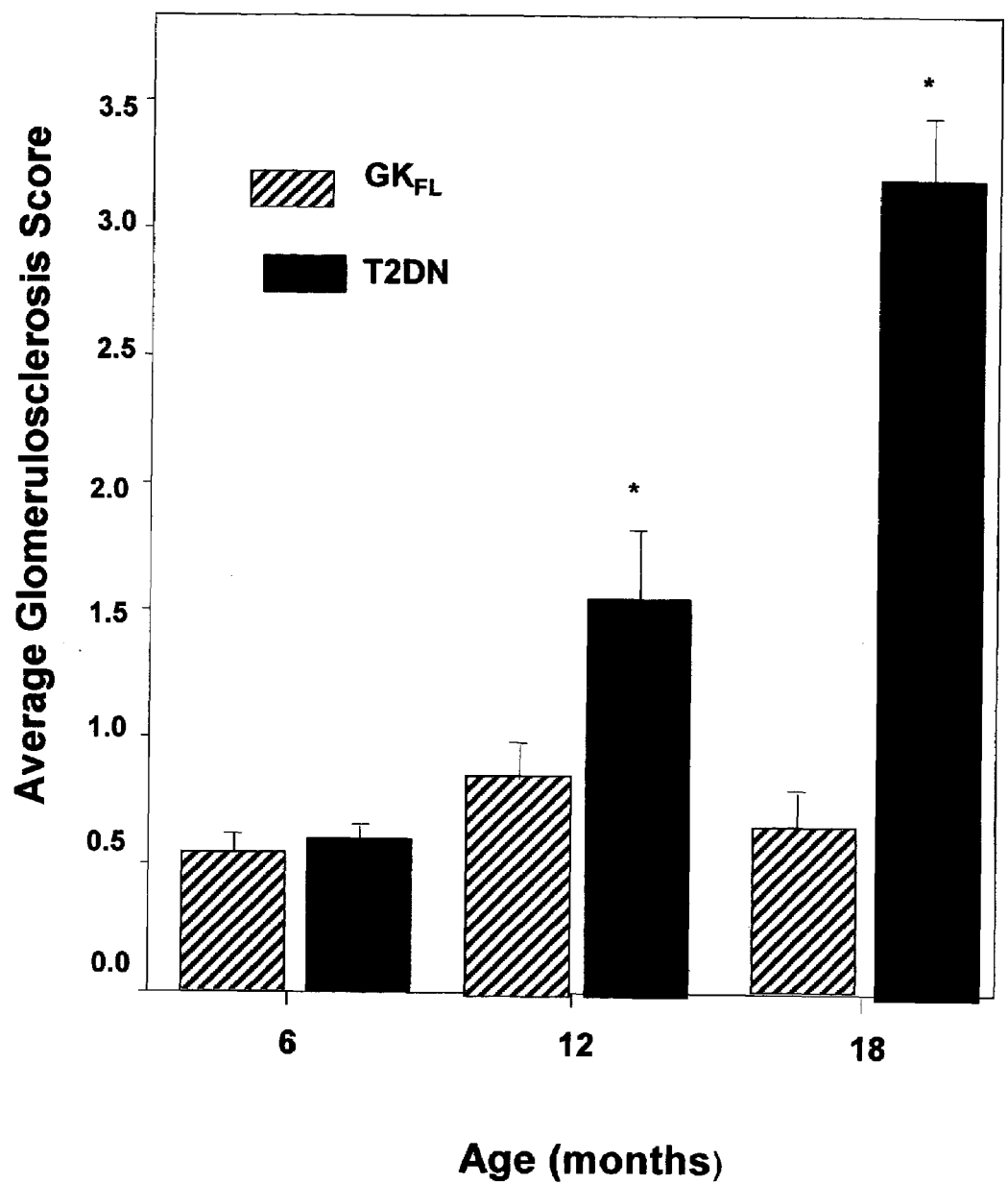
FIG. 10 presents a comparison of the degree of glomerular sclerosis in T2DN mimic and $GK_{FL}$ rats. Scores represent the average injury score (with 0 indicating no damage to capillaries, 2 representing 50% loss of capillary area and 4 representing complete loss of glomerular capillaries) in 30-35 glomeruli scored per kidney. Seven rats in each group were analyzed at 6 months of age. At 12 months, six $GK_{FL}$ and eight T2DN mimic rats were analyzed. At 18 months 4 $GK_{FL}$ and 4 T2DN mimic rats were compared. *=Different from group-matched at 6 months. #=Different from $GK_{FL}$. ($p<0.05$.).
Figure 12:
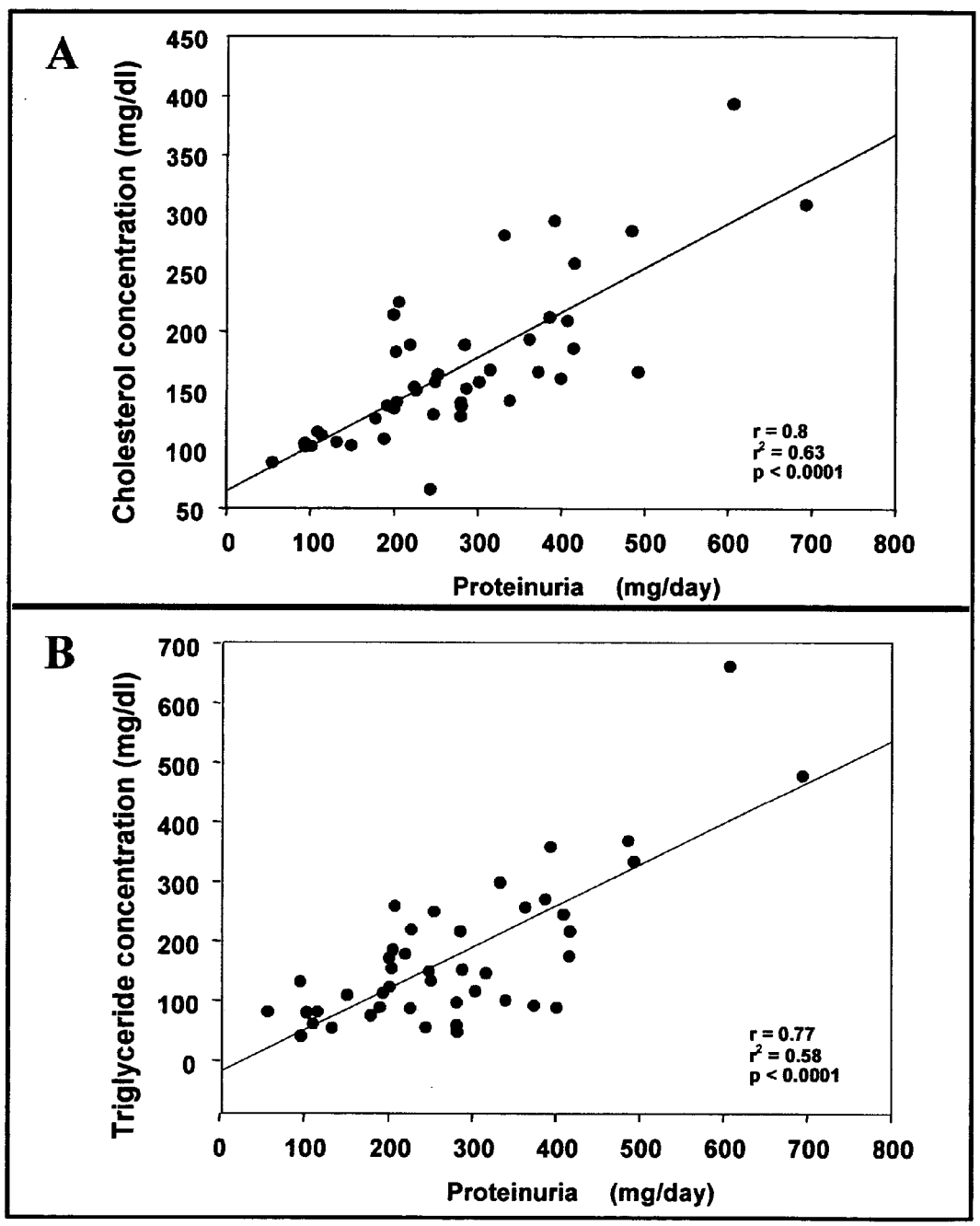
FIG. 12 shows a correlation between proteinuria and dislipidemia in 12 month T2DN mimic rats.

As shown in FIG. 10, 6-month old GK and T2DN mimic strain exhibited a similar degree of glomerulosclerosis (0.51±0.04 and 0.41±0.02, respectively). At the time the rats were 12 months old, the degree of glomerular damage is significantly greater in T2DN mimic than in $GK_{FL}$ rats. At 22-24 months of age T2DN mimic exhibit an almost 100% injury score of 3.5±0.2 while GK rat still exhibit only mild glomerular injury averaging 0.6±0.1, which is similar to that seen in old BN rats.

Dislipidemia

Serum cholesterol levels in 12-month old male T2DN mimic strain rats averaged 170.4±14.0 mg/dL and are four times higher than the levels measured in age-matched male BN rats 41.7±1.4 mg/dL (FIG. 10). Serum triglyceride concentration was also elevated in 12-month old T2DN mimic strain rats (157.6±23.8 mg/dL) compared to the values seen in age-matched control BN rats (34.0±5.1 mg/dL). In 12-month old male GK rats, both serum triglyceride (108±3 mg/dL) and cholesterol levels (66±6 mg/dL) are significantly lower than the corresponding values obtained in age-matched T2DN mimic strain rats. Nevertheless, these values were still elevated relative to those seen in age-matched male BN rats (FIG. 10). The degree of proteinuria and dislipidemia are strongly correlated in T2DN mimic strain rats, as shown in FIG. 11.

DISCUSSION

This present study characterized the development of diabetic nephropathy in a T2DN mimic and $GK_{FL}$ rats that both develop a similar degree of type II diabetes. Following an early onset diabetes, overt proteinuria develops in T2DN mimic strain rats by 6 months of age (>50 mg/day), and the degree of proteinuria progressively becomes more severe as the rats get older. This is accompanied by hypertrophy of the glomerulus, thickening of glomerular and tubular basement membranes, expansion of the mesangial matrix, and the development of focal followed by global glomerulosclerosis and the formation of nodules in many glomeruli by the time T2DN mimic rats are 18 months old. In contrast, $GK_{FL}$ rats exhibit a similar time course of the severity of diabetes, but this strain even at 22 months of age does not develop as severe proteinuria or diabetic glomerulosclerosis with nodule formation even though the kidney does exhibit hypertrophy and thickening of glomerular and tubular basement membranes.

The differences in the development of proteinuria and the severity of glomerular disease between T2DN mimic strain and $GK_{FL}$ rats are most likely due to small differences in genetic background. These rats are genetically identical at 97% of the 543 microsatellites markers tested across the genome. There are a few remaining FHH alleles in the T2DN mimic strain. These alleles contribute about 1% to the genetic difference between the strains.

There are also differences on chromosome 1 between the diabetic susceptible T2DN mimic and diabetic resistant $GK_{FL}$ strain. Five differences in the allele sizes of 5 genetic markers clustered around a 57 cM genomic segment on chromosome 1. The extensive polymorphisms found in this region in an otherwise isogenic background suggests that there is a genetic difference between $GK_{FL}$ and $GK_{Sweden}$ rats that produced the two haplotype forms we now see in T2DN mimic and $GK_{FL}$ strains. This finding is of special importance in the light of previous studies that revealed that there is a quantitative trait loci (QTLs) for type II diabetes in GK rats in general that maps to this region of chromosome 1 (Galli, J., et al., Nat. Genet. 12:31-37, 1996; Gauguier, D., et al., Nat. Genet. 12:38-43, 1996). This QTL, termed Niddm1 has been confirmed in congenic strains to be a major factor in determining hyperglycemia in GK rats (Galli, J., et al., Diabetes 48(12):2463-2470, 1999) but its role in determining the development of renal disease or other diabetic induced end organ damage is unknown.

We found significant enlargement of the glomeruli in both the T2DN mimic strain and $GK_{FL}$ rats at 3 months of age prior to the development of overt proteinuria in T2DN mimic strain rats. These findings seem to corroborate earlier reports that GK rats exhibit glomerular hypertrophy and thickening of basement membrane (Yagihashi, S., et al., Diabetologia 15:309-312, 1978; Phillips, A. O., J. Am. Soc. Neph. 9:639A, 1998; Riley, S. G., et al., J. Lab. Clin. Med. 134(3):304-312, 1999) that is commonly reported in most experimental models of diabetes. The natural course of renal disease in T2DN mimic strain rats closely parallels that of human diabetic nephropathy. Renal structural abnormalities such as glomerular and tubular hypertrophy are already observed at earliest ages and precedes the development of proteinuria. After the development of proteinuria, glomerular and tubular lesions develop that parallel the progression of proteinuria. The most common presentation of glomerular damage in T2DN mimic strain rat at 12 months of age is severe focal segmental glomerulosclerosis, with expansion or the mesangial matrix, obliteration of open glomerular capillary lumens and the formation of nodular lesions in several glomeruli. By the time the rats are 18 months of age, there is further expansion of the mesangial matrix in most glomeruli (severe global sclerosis) and the formation of many large, acellular nodules in many glomeruli. Thus, the presence of nodular glomerulosclerosis is clearly discernible in T2DN mimic strain rats with long-standing (>12 months) diabetes, a pattern in that is consistent with the development of these lesions in patients with diabetes (Olsen, S., Nephrol. Dial. Transplant. 14:1846-1849, 1999; Parving, H. H., et al., "Diabetic Nephropathy," In Brenner and Rector's The Kidney 6$^{th}$ Edition, W. B. Saunders Company, pp. 1731-1773, 2000). The $GK_{FL}$ rats did not develop severe glomerulosclerosis or glomerular nodules even at 22 months in face of severe lifelong diabetes. Thus, the T2DN mimic represents the first animal model of spontaneous diabetes mellitus that develops progressive renal disease with the formation nodular glomerulosclerosis.

Both T2DN mimic strain and $GK_{FL}$ rats develop some degree of dislipidemia, as reflected by elevated levels of serum cholesterol and triglycerides in 12 month old rats. In T2DN mimic strain rats, proteinuria and dislipidemia are strongly correlated. This observation is consistent with previous results in diabetic patients that demonstrate a strong correlation between dislipidemia and progression of diabetic nephropathy (Krolewski, A. S., et al., Kidney Intern. 45(Suppl. 45):S125-S131, 1994;Breyer, J. A., et al., Kidney Intern. 50:1651-1658, 1996). Interestingly, $GK_{FL}$ rats display a milder form of dislipidemia. This likely reflects the milder proteinuria and lack of renal disease observed in these rats. These data seem to support the notion that it is the loss of plasma protein that triggers abnormalities in lipid metabolism due to loss of protein binding and this explains the close association between proteinuria and lipid abnormalities in most forms of ESRD (Keane, W. F., et al., Kidney Intern. 42(Suppl. 38):S134-S138, 1992; O'Donnel, M. P., et al., Am. J. Kidney Dis. 22(1):83-89, 1993; Shohat, J. and Boner, G., Israeli J. Med. Sci. 29:228-239, 1993).

In summary, the present study characterized the first rodent model of spontaneous NIDDM. The T2DN mimic strain that develops progressive proteinuria and glomerulosclerosis which lead to formation of nodules and ESRD. It also identified a closely related control strain of $GK_{FL}$ rats that develops diabetes but is resistant to the development progressive proteinuria and renal disease. There are discrete genetic differences in the autosomes and the mitochondrial genome is completely different between these two strains of rats. It is likely that the genetic differences determine the difference in the susceptibility of the strains to develop diabetic nephropathy in T2DN mimic and $GK_{FL}$ rats. The small genetic differences between the susceptible T2DN mimic and diabetic resistant $GK_{FL}$ strains make this an ideal model for the genetic dissection of diabetes-associated renal disease, as well as dissecting the relationships between the duration and severity of diabetes and the later onset and progression of renal disease.

We claim:

1. A rat diabetes model, wherein the rat develops symptoms of type II diabetes and progressive diabetic nephropathy with nodule formation and wherein the rat is a T2DN rat comprising mitochondrial genome and loci on chromosomes 2 (D2Rat12), 11 (D11Rat93), 16 (D16Rat15), 19 (D19Rat59), and X (DXMit4 and DXMit42) from a Fawn Hooded rat into a GK rat, wherein the T2DN rat does not comprise GK alleles at markers D3Rat57, D11Mgh5, D12Rat22, D1Rat 291, D1Mit18, D1Mit34, D1Mgh12, and D1Rat85, and wherein the T2DN rat develops progressive proteinuria and glomerulosclerosis leading to diabetic nephropathy.

2. The rat of claim 1, wherein the rat is of strain T2DN Mimic$_{MCW}$.

3. The T2DN rat of claim 1 wherein the T2DN rat is further genetically altered by introducing additional genetic material.

4. The T2DN rat of claim 1 wherein the T2DN rat is further genetically altered by introducing genetic deletions.

5. A rat comprising mitochondrial genome and loci on chromosomes 2 (D2Rat12), 11 (D11Rat93), 16 (D16Rat15), 19 (D19Rat59), and X (DXMit4 and DXMit42) from a Fawn Hooded rat into a GK rat, wherein the rat does not comprise GK alleles at markers D3Rat57, D11Mgh5, D12Rat22, D1Rat291, D1Mit18, D1Mit34, D1Mgh12, and D1Rat85, and wherein the rat is obtained by breeding the T2DN rat of claim 1 with a second rat.

6. A rat comprising mitochondrial genome and loci on chromosomes 2 (D2Rat12), 11 (D11Rat93), 16 (D16Rat15), 19 (D19Rat59), and X (DXMit4 and DXMit42) from a Fawn Hooded rat into a GK rat, wherein the rat does not comprise GK alleles at markers D3Rat57, D11Mgh5, D12Rat22, D1Rat291, D1Mit18, D1Mit34, D1Mgh12, and D1Rat85, wherein the rat is obtained by breeding the rat of claim 4 with a second rat.

7. A cell line derived from the rat of claim 1.

8. A cell line derived from the rat of claim 3.

9. A method of evaluating the effect of a test compound on diabetes and diabetic nephropathy in a T2DN rat comprising the steps of:
   (a) exposing the test compound to a T2DN rat comprising mitochondrial genome and loci on chromosomes 2 (D2Rat12), 11 (D11Rat93), 16 (D16Rat15), 19 (D19Rat59), and X (DXMit4 and DXMit42) from a Fawn Hooded rat into a GK rat, wherein the rat does not comprise GK alleles at markers D3Rat57, D11Mgh5, D12Rat22, D1Rat291, D1Mit18, D1Mit34, D1Mgh12, and D1Rat85, and wherein the T2DN rat would develop progressive proteinuria and glomerulosclerosis leading to diabetic nephropathy in the absence of the test compound, and
   (b) comparing the development of diabetes and diabetic nephropathy in the treated T2DN rat with a control T2DN rat which has not been exposed to the test compound.

10. A method of evaluating the effect of a test compound on diabetes and diabetic nephropathy in a T2DN rat comprising the steps of:
    (a) exposing the test compound to a genetically altered T2DN rat comprising mitochondrial genome and loci on chromosomes 2 (D2Rat12), 11 (D11Rat93), 16 (D16Rat15), 19 (D19Rat59), and X (DXMit4 and DXMit42) from a Fawn Hooded rat into a GK rat, wherein the rat does not comprise GK alleles at markers D3Rat57, D11Mgh5, D12Rat22, D1Rat291, D1Mit18, D1Mit34, D1Mgh12, and D1Rat85 and wherein the T2DN rat would develop progressive proteinuria and glomerulosclerosis leading to diabetic nephropathy in the absence of the test compound, and
    (b) comparing the development of diabetes and diabetic nephropathy in the treated genetically altered T2DN rat with a control genetically altered T2DN rat which has not been exposed to the test compound, wherein the treated and the control rats comprise the same genetic modification.

* * * * *

UNITED STATES PATENT AND TRADEMARK OFFICE
CERTIFICATE OF CORRECTION

PATENT NO. : 7,507,871 B2
APPLICATION NO. : 10/625870
DATED : March 24, 2009
INVENTOR(S) : Howard J. Jacob, Richard R. Roman and Marcelo Nobrega It is certified that error appears in the above-identified patent and that said Letters Patent is hereby corrected as shown below:

Column 16, line 50, Claim 3, the second occurrence of "T2DN" in the phrase "The T2DN rat of claim 1 wherein the T2DN rat is further genetically altered by introducing additional genetic material" should be removed. When corrected, line 50 should read: "The T2DN rat of claim 1 wherein the rat is further...".

Column 17, line 12, claim 9, the first occurrence of the word "and" in the phrase "...(D19Rat59), and X (DXMit4 and DXMit42) from a..." should be removed. When corrected, line 12 should read: "...(D19Rat59), X (DXMit4 and DXMit42) from a...".

Column 17, line 16, claim 9, the term "D1Rat85" is incorrect and should be replaced with the term "D1Rat185".

Column 17, line 19, claim 9, the "," in line 19 is incorrect and should be replaced with a ";".

Column 17, lines 20-23, claim 9, the phrase "comparing the development of diabetes and diabetic nephropathy in the treated T2DN rat with a control T2DN rat which has not been exposed to the test compound" is missing the term "genetically altered" in two instances. When corrected, lines 20-23 should read: "comparing the development of diabetes and diabetic nephropathy in the treated genetically altered T2DN rat with a control genetically altered T2DN rat which has not been exposed to the test compound".

Column 18, line 7, claim 10, the first occurrence of the word "and" in the phrase "...(D16Rat15), 19 (D19Rat59), and X (DXMit4 and..." should be removed. When corrected, line 7 should read: "...(D16Rat15), 19 (D19Rat59), X (DXMit4 and...".

Column 18, line 11, claim 10, the term "D1Rat85" is incorrect and should be replaced with the term "D1Rat185".

UNITED STATES PATENT AND TRADEMARK OFFICE
CERTIFICATE OF CORRECTION

PATENT NO. : 7,507,871 B2
APPLICATION NO. : 10/625870
DATED : March 24, 2009
INVENTOR(S) : Howard J. Jacob, Richard R. Roman and Marcelo Nobrega It is certified that error appears in the above-identified patent and that said Letters Patent is hereby corrected as shown below:

Column 18, line 14, claim 10, the "," in line 14 is incorrect and should be replaced with a ";".

Signed and Sealed this

Nineteenth Day of May, 2009

JOHN DOLL
*Acting Director of the United States Patent and Trademark Office*